US009138461B2

(12) United States Patent
Rossomando et al.

(10) Patent No.: US 9,138,461 B2
(45) Date of Patent: Sep. 22, 2015

(54) COMPOSITIONS AND METHODS FOR INCREASING VASCULARIZATION

(71) Applicants: Biogen Idec MA Inc., Cambridge, MA (US); INSERM (Institut National de la Santé et de la Recherche Médicale), Paris (FR)

(72) Inventors: Anthony Rossomando, South Grafton, MA (US); Jean-Sebastien Silvestre, Paris (FR); Radia Tamarat, Paris (FR)

(73) Assignees: Biogen MA Inc., Cambridge, MA (US); INSERM (Institut National de la Santé et de la Recherche Médicale), Paris (FR)

( * ) Notice: Subject to any disclaimer, the term of this patent is extended or adjusted under 35 U.S.C. 154(b) by 0 days.

(21) Appl. No.: 13/679,529

(22) Filed: Nov. 16, 2012

(65) Prior Publication Data

US 2013/0237477 A1 Sep. 12, 2013

Related U.S. Application Data

(62) Division of application No. 12/598,293, filed as application No. PCT/US2008/062265 on May 1, 2008, now Pat. No. 8,329,655.

(60) Provisional application No. 60/915,293, filed on May 1, 2007.

(51) Int. Cl.
*A61K 38/18* (2006.01)
*A61P 9/10* (2006.01)
*A61P 41/00* (2006.01)
*A61K 45/06* (2006.01)
*C07K 14/475* (2006.01)

(52) U.S. Cl.
CPC .............. *A61K 38/185* (2013.01); *A61K 45/06* (2013.01); *C07K 14/475* (2013.01)

(58) Field of Classification Search
None
See application file for complete search history.

(56) References Cited

U.S. PATENT DOCUMENTS

| | | |
|---|---|---|
| 4,352,883 A | 10/1982 | Lim |
| 4,353,888 A | 10/1982 | Sefton |
| 4,407,957 A | 10/1983 | Lim |
| 4,883,666 A | 11/1989 | Sabel et al. |
| 4,968,733 A | 11/1990 | Muller et al. |
| 4,976,859 A | 12/1990 | Wechs |
| 5,084,350 A | 1/1992 | Chang et al. |
| 5,158,881 A | 10/1992 | Aebischer et al. |
| 5,194,596 A | 3/1993 | Tischer et al. |
| 5,284,761 A | 2/1994 | Aebischer et al. |
| 5,350,836 A | 9/1994 | Kopchick et al. |
| 5,414,135 A | 5/1995 | Snow et al. |
| 5,445,934 A | 8/1995 | Fodor et al. |
| 5,496,804 A | 3/1996 | Reed et al. |
| 5,525,464 A | 6/1996 | Drmanac et al. |
| 5,618,531 A | 4/1997 | Cherksey |
| 5,641,749 A | 6/1997 | Yan et al. |
| 5,650,494 A | 7/1997 | Cerletti et al. |
| 5,654,007 A | 8/1997 | Johnson et al. |
| 5,733,729 A | 3/1998 | Lipshutz et al. |
| 5,754,524 A | 5/1998 | Wark |
| 5,770,577 A | 6/1998 | Kinstler et al. |
| 5,775,320 A | 7/1998 | Patton et al. |
| 5,780,014 A | 7/1998 | Eljamal et al. |
| 5,780,019 A | 7/1998 | Klier et al. |
| 5,785,049 A | 7/1998 | Smith et al. |
| 5,795,716 A | 8/1998 | Chee et al. |
| 5,798,113 A | 8/1998 | Dionne et al. |
| 5,800,992 A | 9/1998 | Fodor et al. |
| 5,814,607 A | 9/1998 | Patton |
| 5,834,029 A | 11/1998 | Bellamkonda et al. |
| 5,846,935 A | 12/1998 | Panayotatos |
| 5,916,555 A | 6/1999 | Lee et al. |
| 5,939,524 A | 8/1999 | Bowditch et al. |
| 6,063,757 A | 5/2000 | Urso |
| 6,083,725 A | 7/2000 | Selden et al. |
| 6,084,076 A | 7/2000 | Ejima et al. |
| 6,284,540 B1 | 9/2001 | Milbrandt et al. |
| 6,299,895 B1 | 10/2001 | Hammang et al. |
| 6,361,771 B1 | 3/2002 | Tao et al. |
| 6,593,133 B1 | 7/2003 | Johansen et al. |
| 6,677,135 B1 | 1/2004 | Sanicola-Nadel et al. |
| 6,723,344 B2 | 4/2004 | Sakiyama-Elbert et al. |
| 6,734,284 B1 | 5/2004 | Johansen et al. |

(Continued)

FOREIGN PATENT DOCUMENTS

| | | |
|---|---|---|
| EP | 1 373 503 | 11/2007 |
| EP | 1 930 439 | 6/2008 |

(Continued)

OTHER PUBLICATIONS

Iozzo, "Matrix Proteoglycans: From Molecular Design to Cellular Function," Ann Rev Biochem., 1998, 67:609-52.

Partial European Search Report for Application No. EP 07 12 0461, completed Apr. 29, 2008, 5 pages.

International Search Report, PCT/DK2006/000572, mailed on May 7, 2007, 2 pages.

International Search Report, PCT/EP02/02691, mailed Dec. 20, 2002, 5 pages.

(Continued)

*Primary Examiner* — Zachary Howard

(74) *Attorney, Agent, or Firm* — Fish & Richardson P.C.

(57) ABSTRACT

Disclosed are methods of increasing vascularization in a tissue by administering a neublastin polypeptide to a mammal exhibiting impaired or inadequate blood flow in the tissue. The methods can be used to in the treatment or prevention of a disorder characterized by impaired or inadequate blood flow or to increase vascularization in an organ that has been transplanted into a subject.

15 Claims, 3 Drawing Sheets

(56) References Cited

U.S. PATENT DOCUMENTS

| | | | |
|---|---|---|---|
| 7,067,473 | B1 | 6/2006 | Masure |
| 7,115,257 | B1 | 10/2006 | Tao et al. |
| 7,276,580 | B2 | 10/2007 | Sah et al. |
| 7,358,228 | B2 | 4/2008 | Sah et al. |
| 7,442,370 | B2 | 10/2008 | Sah et al. |
| 7,598,059 | B2 | 10/2009 | Pederson et al. |
| 7,601,518 | B2 | 10/2009 | Wahlberg et al. |
| 7,655,463 | B2 | 2/2010 | Sah et al. |
| 8,119,114 | B2 | 2/2012 | Sah et al. |
| 8,163,875 | B2 | 4/2012 | Sah et al. |
| 8,217,146 | B2 | 7/2012 | Sah et al. |
| 8,263,553 | B2 | 9/2012 | Rossomando et al. |
| 8,329,655 | B2 | 12/2012 | Rossomando et al. |
| 8,642,732 | B2 | 2/2014 | Sah et al. |
| 8,722,862 | B2 | 5/2014 | Rossomando et al. |
| 2002/0002263 | A1 | 1/2002 | Milbrandt et al. |
| 2002/0002269 | A1 | 1/2002 | Milbrandt et al. |
| 2002/0055467 | A1 | 5/2002 | Johansen et al. |
| 2002/0114780 | A1 | 8/2002 | Bankiewicz et al. |
| 2002/0192209 | A1 | 12/2002 | Baker et al. |
| 2003/0059868 | A1 | 3/2003 | Greenwood et al. |
| 2003/0078373 | A1 | 4/2003 | Fersht et al. |
| 2003/0100497 | A1 | 5/2003 | Baker et al. |
| 2003/0166537 | A1 | 9/2003 | Hanke |
| 2003/0186267 | A1 | 10/2003 | Feder et al. |
| 2004/0028613 | A1 | 2/2004 | Quay |
| 2004/0077543 | A1 | 4/2004 | Sah et al. |
| 2004/0142418 | A1 | 7/2004 | Sah et al. |
| 2004/0230043 | A1 | 11/2004 | Johansen et al. |
| 2004/0242472 | A1 | 12/2004 | Shelton et al. |
| 2004/0265972 | A1 | 12/2004 | Weintraub et al. |
| 2005/0069520 | A1 | 3/2005 | Shi et al. |
| 2005/0089960 | A1 | 4/2005 | Wahlberg et al. |
| 2005/0118157 | A1 | 6/2005 | McMahon et al. |
| 2005/0142098 | A1 | 6/2005 | Sah et al. |
| 2005/0158824 | A1 | 7/2005 | Pedersen et al. |
| 2005/0180957 | A1 | 8/2005 | Scharp et al. |
| 2005/0181991 | A1 | 8/2005 | Shelton et al. |
| 2005/0233359 | A1 | 10/2005 | Masure et al. |
| 2006/0009625 | A1 | 1/2006 | Bedows et al. |
| 2006/0014288 | A1 | 1/2006 | Kim et al. |
| 2006/0122135 | A1 | 6/2006 | Geerts et al. |
| 2006/0165667 | A1 | 7/2006 | Laughlin et al. |
| 2007/0099270 | A1 | 5/2007 | Sah et al. |
| 2007/0238670 | A1 | 10/2007 | Sah et al. |
| 2007/0254842 | A1 | 11/2007 | Bankiewicz |
| 2008/0039385 | A1 | 2/2008 | Rossomando et al. |
| 2008/0227703 | A1 | 9/2008 | Johansen et al. |
| 2008/0249287 | A1 | 10/2008 | Rossomando et al. |
| 2008/0260702 | A1 | 10/2008 | Jorgensen |
| 2008/0306212 | A1 | 12/2008 | Sah et al. |
| 2009/0221495 | A1 | 9/2009 | Rossomando et al. |
| 2009/0258831 | A1 | 10/2009 | Sah |
| 2010/0056440 | A1 | 3/2010 | Rossomando et al. |
| 2010/0234293 | A1 | 9/2010 | Johansen et al. |
| 2010/0261654 | A1 | 10/2010 | Rossomando et al. |
| 2010/0292142 | A1 | 11/2010 | Sah et al. |
| 2011/0135648 | A1 | 6/2011 | Rossomando et al. |
| 2012/0252726 | A1 | 10/2012 | Johansen et al. |
| 2012/0316109 | A1 | 12/2012 | Sah et al. |
| 2013/0096065 | A1 | 4/2013 | Rossomando et al. |
| 2013/0109624 | A1 | 5/2013 | Sah et al. |

FOREIGN PATENT DOCUMENTS

| | | |
|---|---|---|
| JP | 11-310600 | 11/1999 |
| JP | 2002-534957 | 10/2002 |
| JP | 2003-310258 | 11/2003 |
| RU | 2225728 | 8/1999 |
| WO | WO 92/19195 | 11/1992 |
| WO | WO 93/06116 | 4/1993 |
| WO | WO 95/05452 | 2/1995 |
| WO | WO 97/08196 | 3/1997 |
| WO | WO 97/11964 | 4/1997 |
| WO | WO 97/19693 | 6/1997 |
| WO | WO 98/32869 | 7/1998 |
| WO | WO 99/03887 | 1/1999 |
| WO | WO 99/13090 | 3/1999 |
| WO | WO 99/42486 | 8/1999 |
| WO | WO 99/43813 | 9/1999 |
| WO | WO 99/49039 | 9/1999 |
| WO | WO 00/01815 | 1/2000 |
| WO | WO 00/04050 | 1/2000 |
| WO | WO 00/15665 | 3/2000 |
| WO | WO 00/17360 | 3/2000 |
| WO | WO 00/18799 | 4/2000 |
| WO | WO 00/34475 | 6/2000 |
| WO | WO 00/73348 | 12/2000 |
| WO | WO 01/47946 | 7/2001 |
| WO | WO 01/53486 | 7/2001 |
| WO | WO 01/66164 | 9/2001 |
| WO | WO 01/76639 | 10/2001 |
| WO | WO 01/87925 | 11/2001 |
| WO | WO 02/46430 | 6/2002 |
| WO | WO 02/051433 | 7/2002 |
| WO | WO 02/060929 | 8/2002 |
| WO | WO 02/072826 | 9/2002 |
| WO | WO 02/078730 | 10/2002 |
| WO | WO 03/044055 | 5/2003 |
| WO | WO 2004/002763 | 1/2004 |
| WO | WO 2004/069176 | 8/2004 |
| WO | WO 2004/094592 | 11/2004 |
| WO | WO 2004/108760 | 12/2004 |
| WO | WO 2005/039643 | 5/2005 |
| WO | WO 2006/023781 | 3/2006 |
| WO | WO 2006/023782 | 3/2006 |
| WO | WO 2007/042040 | 4/2007 |
| WO | WO 2007/100898 | 9/2007 |
| WO | WO 2007/103182 | 9/2007 |
| WO | WO 2008/137574 | 11/2008 |
| WO | WO 2009/020964 | 2/2009 |

OTHER PUBLICATIONS

International Search Report, PCT/DK99/00384, mailed on Dec. 29, 1999, 3 pages.

Extended European Search Report for EP Application No. 10181304.6, dated Aug. 5, 2011, 16 pages.

Extended European Search Report for EP Application No. 131561649, dated Jun. 17, 2013, 9 pages.

GenBank Accession No. AF067197, Li, 1998, 2 pages.

Ishai-Michaeli et al.,, "Importance of Size and Sulfation of Heparin in Release of Basic Fibroblast Growth Factor from the Vascular Endothelium and Extracellular Matrix," Biochem., 1992, 31:2080-2088.

Rickard et al., "The binding of human glial cell line-derived neurotrophic factor to heparin and heparan sulfate: importance of 2-O-sulfate groups and effect on its interaction with its receptor, GFRα1," Glycobiology, 2003, 13:419-426.

Abrams et al., "Emerging strategies to promote improved functional outcome after peripheral nerve injury," Restor. Neurol. Neurosci., 23(5-6):367-82 (2005).

Aebischer et al, "Recombinant proteins for neurodegenerative diseases: the delivery issue," Trends in Neuroscience, Elsevier, Amsterdam, NL 24(9):533-540 (2001).

Aebischer et al., "Intrathecal delivery of CNTF using encapsulated genetically modified xenogeneic cells in amyotrophic lateral sclerosis patients," Nature Medicine, 2:696-699 (1996).

Airaksinen et al., GDNF family neurotrophic factor signaling: four masters, one servant, Mol. Cell Neurosci., 13:313-325 (1999).

Airaksinen et al., "The GDNF family: signalling, biological functions and therapeutic value," Nature Reviews, Neuroscience 3:383-394 (May 2002).

Alfano et al., "The major determinant of the heparin binding of glial cell-line-derived neurotrophic factor is near the N-terminus and is dispensable for receptor binding," Biochem. J., 404(1):131-40 (2007).

Algvere et al., "Transplantation of RPE in age-related macular degeneration: observations in disciform lesions and dry RPE atrophy," Graefe's Arch. Clin. Exp. Ophthalmol., 235:149-158 (1997).

Anderson, "Human gene therapy," Nature, 392:25-30 (1998).

(56) References Cited

OTHER PUBLICATIONS

Andres et al., "Multiple effects of artemin on sympathetic neurone generation, survival and growth," Development 128:3685-3695 (2001).
Anonymous, "Anti-human Artemin Antibody," R&D Systems Product Data Sheets (Dec. 27, 2006), [online] XP002505114. Retrieved from the Internet: http://www.rndsystems.com/pdf/AF2589.pdf [retrieved on Nov. 21, 2008].
Anonymous, "L-arginine entry," Drugs.com drug information online, 15 pp as printed (2009).
Anonymous, "Monoclonal Anti-human Artemin Antibody," R&D Systems Product Data Sheets (Mar. 23, 2006), [online] XP002505115. Retrieved from the Internet: http://www.rndsystems.com/pdf/MAB2589.pdf [retrieved on Nov. 21, 2008].
Atschul et al., "Gapped BLAST and PSI-BLAST: a new generation of protein database search programs," Nucl. Acids Res., 25:3389-3402 (1997).
Baloh et al. "Artemin, a novel member of the GDNF ligand family, supports peripheral and central neurons and signals through the GFRalpha3-RET receptor complex," Neuron, 21(6):1291-1302 (1998).
Baloh et al., "Functional mapping of receptor specificity domains of glial cell line-derived neurothropic factor (GDNF) family ligands and production of GFR alpha 1 RET-specific agonists," J. of Biological Chemistry, 275(5):3412-3420 (2000).
Baudet et al., "Positive and negative interactions of GDNF, NTN and ART in developing sensory neuron subpopulations, and their collaboration with neurotrophins," Development, 127:4335-4344 (2000).
Bauskin et al., "The propeptide of macrophage inhibitory cytokine (MIC-1), a TGF-β superfamily member, acts as a quality control determinant for correctly folded MIC-1," The EMBO Journal, 19(10):2212-2220 (2000).
Bendtsen et al., "Improved prediction of signal peptides—SignalP 3.0," J. Mol. Biol., 340(4):783-795 (2004).
Bennett et al., "Artemin has potent neurotrophic actions on injured C-fibres," J. Peripher. Nerv. Syst., 11(4):330-45 (2006).
Bennett et al., "A distinct subgroup of small DRG cells express GDNF receptor components and GDNF is protective for these neurons after nerve injury," J. Neurosci. 18(8):3059-3072 (Apr. 15, 1998).
Bennett, G., "An animal model of neuropathic pain: A review," Muscle & Nerve 16:1040-1048 (1993).
Bonde et al., "GDNF and neublastin protect against NMDA-induced excitotoxicity in hipocampal slice cultures," Neuroreport., 11:4069-4073 (2000).
Bootcov et al., "MIC-1, a novel macrophage inhibitory cytokine, is a divergent member of the TGF-β superfamily," Pro. Natl. Acad. Sci. U.S.A., 94:11514-11519 (1997).
Bork, "Go hunting in sequence databases but watch out of the traps," Trends in Genetics, 12:425-427 (1996).
Bork, "Powers and Pitfalls in Sequence analysis: the 70% Hurdle," Genome Research, 10:398-400 (2000).
Borodovsky et al., "Detection of new genes in a bacterial genome using Markov models for three gene classes," Nucl. Acids Res., 23:3554-3562 (1995).
Boucher et al "Artemin prevents injury-induced changes in small sensory neurons," Abstracts of the Society for Neuroscience, Society for Neuroscience, Washington D.C. 26(1/2):63305 (2000).
Brenner, "Errors in genome annotation," Trends in Genetics, 15:132-133 (1999).
Burgess et al., "Possible dissociation of the heparin-binding and mitogenic activities of heparin-binding (acidic fibroblast) growth factor-1 from its receptor-binding activities by site-directed mutagenesis of a single lysine residue," J. of Cell Biology, 111:2129-2138 (1990).
Callister et al., Soc. for Neuroscience Abstracts 27(1):36.11 (2001).
Campbell et al., "Mechanisms of Neuropathic Pain," Neuron, 52:77-92 (2006).

Carmillo et al., "Glial Cell Line-Derived Neurotrophic Factor (GDNF) Receptor α-1(GFRα1) Is Highly Selective for GDNF versus Artemin," Biochemistry, 44:2545-2554 (2005).
Ceyhan et al., "The neurotrophic factor artemin promotes pancreatic cancer invasion," Ann. Surg., 244:274-81 (2006).
Ceyhan et al., "The neurotrophic factor artemin influences the extent of neural damage and growth in chronic pancreatitis," Gut., 56(4):534-44 (2007).
Damon et al., "Vascular-derived artemin: a determinant of vascular sympathetic innervation?," Am. J. Physiol. Heart Circ. Physiol., 293:H266-H273 (2007).
Daopin et al., "Crystal structure of TGF-J2 refined at 1.8 A resolution," Proteins, 17:176-192 (1993).
Delgado et al., "The uses and properties of PEG-Linked proteins, Critical Reviews in Therapeutic Drug Carrier Systems," 9(3/4):249-304 (1992).
Doerks et al., "Protein annotation: detective work for function prediction," Trends in Genetics, 14:248-250 (1998).
During et al., "Towards gene therapy for the central nervous system," Mol. Med., 11:485-493 (1998).
Eigenbrot et al., "X-ray structure of glial cell-derived neurotrophic factor at 1 9 A resolution and implications for receptor binding," Nat. Struct. Biol., 4:435-438 (1997).
Enomoto et al., "RET signaling is essential for migration, axonal growth and axon guidance of developing sympathetic neurons," Development, 128:3963-3974 (2001).
Enzmann et al., "Immunological problems of transplantation into the subretinal space," Acta Anat., 162:178-183 (1998).
Fairlie et al., "The propeptide of the transforming growth factor-β superfamily member, macrophage inhibitory cytokine-1 (MIC-1), is a multifunctional domain that can facilitate protein folding and secretion," J. of Biol. Chem., 276(20):16911-16918 (2001).
Fargrell, B. et al., "Disburbed microvascular reactivity and shunting—a major cause for diabetic complications," Vascular Medicine (1999); 4:125-127.
Finsen et al., "Somatostatin and neuropeptide Y in organotypic slice cultures of the rat hippocampus: an immunocytochemical and in situ hybridization study," Neurosci., 47:105-113 (1992).
Fjord-Larsen, et al. "Efficient in vivo protection of nigral dopaminergic neurons by lentiviral gene transfer of a modified Neurturin construct," Experimental Neurology, 195:49-60 (2005).
Flanders et al., "TGFβ," Laboratory of Cell Regulation and Carcinogenesis, National Cancer Institute, 719-746 (undated).
Francis et al., "Pegylation of Cytokines and other therapeutic proteins and peptides: the importance of biological optimization of coupling techniques," Int'l. Journal of Hematology, Elsevier Science Publishers, NL., 68(1):1-18 (1998).
Frankel et al., "High-Level Expression and Purifcation of the Recombinant Diphtheria Fusion Toxin DTGM for Phase I Clinical Trials," Expr Purif. 16(1):190-201, (Jun. 1999).
Freynhagen et al., "The evaluation of neuropathic components in law back pain," Current Pain & Headache Reports 13:185-190 (2009).
Friedmann, "Principles for human gene therapy studies," Science, 287:2163-2164 (2000).
Gardell et al., "Multiple actions of systemic artemin in experimental neuropathy," Nat Med., 9(11):1383-89 (2003).
GenBank Accession No. AA844072, 2 pages (1998).
GenBank Accession No. AC005037, Waterston, 54 pages (1998).
GenBank Accession No. AC005038, Sulston et al., 96 pages (2001).
GenBank Accession No. AC005051, Waterston, 38 pages (1998).
GenBank Accession No. AF109402 (1998).
GenBank Accession No. AF040962, Milbrandt et al., 2 pages (1998).
Genbank Accession No. AF120274, Rosenblad et al., 3 pages (1999).
Gilchuk, "Assessment of renaturation methods for industrial producing recombinant proteins in biologically active form from E. coli inclusion bodies," Biopolymers and Cell, 20(3):182-192 (2004).
Griffin et al., "Assessment of cutaneous innervation by skin biopsies," Current Opinion in Neurology, 14:655-659 (2001).
Guerra et al., "PEGylation prevents the N-terminal degradation of megakaryocyte growth and development factor," Pharm. Res., 15(12):1822-1827 (1998).
Gustafsson, "New insights in oestrogen receptor (ER) research—the ERbeta," Eur. J. Cancer, 36 Suppl. 4:S16 (2000).

(56) References Cited

OTHER PUBLICATIONS

Hall et al., "Eukaryotic and Prokaryotic Signal Peptides Direct Secretion of a Bacterial Endoglucanase by Mammalian Cells," Journal of Biological Chemistry, 265(32):19996-19999 (1990).

Hallböök et al., "Expression of Neurotrophins and Trk Receptors in the Avian Retina," J. Compar. Neurol., 364:664-676 (1996).

Hamilton et al., "Heparin coinfusion during convection-enhanced delivery (CED) increases the distribution of the glial-derived neurotrophic factor (GDNF) ligand family in rat striatum and enhances the pharmacological activity of neurturin," Experimental Neurology, 168:155-161 (2001).

Hoane et al. "Mammalian-Cell-Produced Neurturin (NTN) Is More Potent Than Purified *Escherichia coli*-Produced NTN," Exp. Neurol., 162:189-193 (2000).

Honma, Y. et al., "Artemin is a vascular-derived neurotrophic factor for developing sympathetic neurons," Neuron 35(2):267-282, 2002.

Israel et al., "Acetylcholine Release and the Cholinergic Genomic Locus," Molecular Neurobio., 16(1):1-20 (1998).

Johansen et al., "Biosynthesis of peptide precursors and protease inhibitors using new consititutive and inducible eukaryotic expression vectors," FEBS Lett., 267:289-294 (1990).

Kim et al., "An experimental model for peripheral neuropathy produced by segmental spinal nerve ligation in the rat," Pain, 50:355-363 (1992).

Kirsch et al. "Expression of ciliary neurotrophic factor receptor mRNA and protein in the early postnatal and adult rat nervous system," Neurosci. Lett., 180:163-166 (1994).

Kotzbauer et al., "Neurturin, a relative of glial-cell-line-derived neurotrophic factor," Nature, 384:467-70 (1996).

Kron et al., "Coronary revascularization rather than cardiac transplantation for chronic ischemic cardiomyopathy," Ann. Surg., 210:348-352 (1989).

Lapchak et al., "Pharmacological characterization of glial cell line-derived neurotrophic factor (GDNF): implications for GDNF as a therapeutic molecule for treating neurodegenerative diseases," Cell Tissue Res., 286:179-189 (1996).

Lapchak, "Therapeutic potential for glial cell line-derived neurotropic factor (GDNF) based upon pharmacological activities in the CNS," Rev. Neurosci., 7:165-176 (1977).

Lavail et al., "Protection of mouse photoreceptors by survival factors in retinal degenerations," Invest. Ophthalmol. Vis. Sci., 39(3):592-602 (1998).

Lee et al., "Proliferin Secreted by Cultured Cells Binds to Mannose 6-Phosphate", J. Biol. Chem., 263(7):3521-3527 (1988).

Lee et al., "Prolonged circulating lives of single-chain Fv proteins conjugated with polyethylene glycol: a comparison of conjugation chemistries and compounds," Bioconjug. Chem., 10:973-981 (1999).

Li et al., "Beta-Endorphin omission analogs: dissociation of immunoreactivity from other biological activities," PNAS, 77(6):3211-14 (1980).

Li et al., "Expression, purification, and characterization of recombinant human neurturin secreted from the yeast Pichia pastoris," Protein Expression and Purification, 30(1):11-17 (2003).

Lin et al., "GDNF: A glial cell line-derived neurotrophic factor for midbrain dopaminergic neurons," Science, 260:1130-1132 (1993).

Little et al., "Transplantation of human fetal retinal pigment epithelium rescues photoreceptor cells from degeneration in the royal college of surgeons rat retina," Invest. Ophthalmol. Vis. Sci., 37(1):204-211 (1996).

Lorenz et al., "Heteromultimeric CLC chloride channels with novel properties," Proc. Natl. Acad. Sci USA, 93:13362-13366 (1996).

Machelska et al., "Breaking the pain barrier," Nature Medicine 9(11):1353-1354 (2003).

Maeda et al., "Efficient Production of Active TNF I By albumin Signal Peptide," Biochemistry and Molecular Biology International, Academic Press, London, GB, 42(4):825-832 (1997).

Massague et al., "The TGF-J family and its composite receptor," Trends Cell Biol., 4:172-178 (1994).

Mason, "The RET receptor tyrosine kinase: activation, signalling and significance in neural development and disease," Pharm. Acta. Helv., 74:261-4 (2000).

Masure et al., "Enovin, a novel member of the GDNF family of neurotrophic growth factors with growth promoting and neuroprotective effects on neuronal cells," a poster presentation from Janssen Research Foundation, "Gordon Conference" held on Jun. 6-11, 1999.

Masure, et al., "Enovin, a member of the glial cell-line-derived neurotrophic factor (GDNF) family with growth promoting activity on neuronal cells," Eur J. Biochem., 266:892-902 (1999).

Masure et al., "Mammalian GFRalpha-4, a divergent member of the GFRalpha family of coreceptors for glial cell line-derived neurotrophic factor family ligands, is a receptor for the neurotrophic factor persephin," J. Biol. Chem., 275:39427-34 (2000).

Matsushita et al., "Cloning and structural organization of the gene encoding the mouse glial cell line-derived neurotrophic factor, GDNF," Gene, 203:149-157 (1997).

McDonald et al., "A structural superfamily of growth factors containing a cystine knot motif.," Cell, 73:421-424 (1993).

Merlo et al. "The Mouse int-2 Gene Exhibits Basic Fribroblast Growth Facctor Activity in a Basic Fibroblast Growth Factor-responsive Cell Line," Cell Growth & Differentiation, 1:463-472 (1990).

Milbrandt et al., "Persephin, a novel neurotrophic factor related to GDNF and Neurturin," Neuron, 20:245-253 (1998).

Mills, C.D. et al., "Strain and Model differences in behavioral outcomes after spinal cord injury in rat," J. Neurotrauma 18(8):743-56 (2001).

Mogyoros et al., "Strength-duration properties of sensory and motor axons in amyotrophic lateral sclerosis," Brain 121:851-859 (1998).

Moore et al., "Renal and neuronal abnormalities in mice lacking GDNF," Nature, 382:76-79 (1996).

Moustakas et al., "Smad regulation in TGF-$\beta$ signal transduction," J. of Cell Science, 114:4359-4369 (2001).

Ngo et al., "The Protein Folding Problem and Tertiary Structure Prediction," Birkhäuser, 492-495 (1994).

Nielsen et al., "Identification of prokaryotic and eukaryotic signal peptides and prediction of their cleavage sites," Protein Engineering, 10(1):1-6 (1997).

Nielsen et al., "Prediction of signal peptides and signal anchors by a hidden Markov model," Proceedings of the 6th International Conference on Intelligent systems for Molecular Biology, 122-130 (1998).

Nishino et al., "GFR alpha3, a component of the artemin receptor, is required for migration and survival of the superior cervical ganglion," Neuron, 23(4):725-736 (1999).

Norton et al., "Bacterial beta-Galactosidase as a Marker of Rous Sarcoma Virus Gene Expression and Replication," Mol. Cell. Biol., 5:281-290 (1985).

Orozco et al., "Nociceptive Neurons Express GFR$\alpha$3," Society for Neuroscience, Abstracts 26 (1-2): Abstract No. 412.7 (2000).

Orozco et al., "GFRalpha3 is expressed predominantly in nociceptive sensory neurons," Eur. J. Neurosci., 13(11):2177-82 (2001).

Palmiter, "Heterologous introns can enhance expression of transgenes in mice," PNAS, 88:478-482 (1991).

Park et al., "Coordinated interaction of the vascular and nervous systems: from molecule- to cell-based approaches," Biochem. Biophys. Res. Commun., 311:247-253 (311) (2003).

Park et al., "Tarnscriptional regulation of artemin is related to neurite outgrowth and actin polymerization in mature DRG neurons," Neuroscience Letters 404:61-66 (2006).

Pawson et al., "Assembly of cell regulatory systems through protein interaction domains," Science, 300:445-452 (2003).

PIR_80 Accession No. 14968.

Pons et al., "Massive cortical reorganization after sensory deafferentation in adult macaques," Scient. 252(5014):1857-1860 (1991).

Purves, D. et al., "The Cover, Dorsal view of the human brain," Neuroscience, Sinauer Associates, Inc., $2^{nd}$ Ed., pp. 75, 367, 400, 403, 554, 555, and 678 (2001).

Rakowicz et al., "Glial Cell Line-Derived Neurotrophic Factor Promotes the Survival of Early Postnatal Spinal Motor Neurons in the Lateral and Medial Motor Columns in Slice Culture," The Journal of Neuroscience, 22(10):3953-3962 (2002).

(56) References Cited

OTHER PUBLICATIONS

Ramachandran et al., "Perceptual correlates of massive cortical reorganization," Science 258(5085):1159-1160 (1992).
Ramachandran, "Behavioral and MEG correlates of neural plasticity in the adult human brain," Proceedings of the National Academy of Sciences 90:10413-10420 (1993).
Ramer et al., "Functional regeneration of sensory axons into the adult spinal cord," Nature 403:312-316 (Jan. 2000).
Rattenholl et al., "Pro-sequence assisted folding and disulfide bond formation of human nerve growth factor," J. Mol. Biol., 305:523-533 (2001).
Rattenholl et al., "The pro-sequence facilitates folding of human nerve growth factor from *Escherichia coli* inclusion bodies," Eur. J. Biochem., 268:3296-3303 (2001).
Reddy, "Controlled-release peylation, liposomal formulations: new mechanisms in the delivery of injectable drugs," Annals of Pharmacotherapy, 34(7/8):915-923 (2000).
Reinshagen et al., "Commercial recombinant human β-Nerve Growth factor and adult rat dorsal root ganglia contain an identical molecular species of nerve growth factor prohormone," J. of Neurochemistry, 74:2127-2133 (2000).
Rico et al., "Characterization of the immunostimulatory properties of Leishmania infantum HSP70 by fusion to the *Escherichia coli* maltose-binding protein in normal and nu/nu BALB/c mice," Infect Immun. 66:1347-352 (Jan. 1998).
Riganti et al., "Nitroarginine methyl ester and canavanine lower intracellular reduced glutathione," Free Radic. Biol. Med., 35(10):1210-6 (2003).
Robertson et al., "The GDNF-RET signaling in partnership," Trends Genet., 13:1-3 (1997).
Rosenberg et al., "Gene therapist, heal thyself," Science, 287:1751 (2000).
Rosenberg et al., "Vectors for selective expression of cloned DNAs by T7 RNA polymerase," Gene, 56:125-135 (1987).
Rosenblad et al., "In vivo protection of nigral dopamine neurons by lentiviral gene transfer of the novel GDNF-family member neublastin/artemin," Molecular and Cellular Neuroscience, 15(2):199-214 (2000).
Rosenblad et al., "In vivo protection of nigral dopamine neurons by lentiviral gene transfer of the novel GDNF-family member neublastin/artemin," Mol. Cell Neurosci., 18(3):332-333 (2001).
Rossomando et al., "In vitro and in vivo characterization of neublastin, a nociceptive neuronal trophic factor," Abstracts of the Annual Meeting of the Society for Neuroscience, Society for Neuroscience, Washington, DC, U.S., 27(1):361 (2001) (XP001121851, ISSN: 0190-5295).
Saarma et al., "Other neurotrophic factors: glial cell line-derived neurotrophic factor (GDNF)," Microsc. Res. Tech., 45(4-5):292-302 (1999).
Saarma, "GDNF: A stranger in the TGF-beta superfamily?" European Journal of Biochemistry, 267(24):6968-6971 (2000).
Sadick et al., "Analysis of heregulin-induced ErbB2 phosphorylation with a high-throughput Kinase receptor activation enzyme-linked immunosorbant assay," Anal. Biochem., 235(2):207-14 (1996).
Sah et al., "Prevention and Reversal of Experimental Neuropathic Pain by Systemic Neublastin," Society for Neuroscience Abstracts, 27(1):361 (2001).
Sah et al., "Neurotrophic factors as novel therapeutics for neuropathic pain," Nature Reviews 2:460-472 (2003).
Sah et al., "New approaches for the treatment of pain: the GDNF family of neurotrophic growth factors," Curr. Top Med. Chem., 5(6):577-83 (2005).
Sanicola et al., "Glial cell line-derived neurotrophic factor-dependent RET activation can be mediated by two different cell-surface accessory proteins," Proc Natl Acad Sci, USA, 94:6238-6243 (1997).
Sauer et al., "Progressive degeneration of nigrostriatal dopamine neurons following intrastraiatal terminal lesions with 6-hydroxydopamine: a combined retrograde tracing and immunocytochemical study in the rat," Neuroscience, 59:401-415 (1994).
Schmidt et al. "In vivo kinetics as a sensitive method for testing physiologically intact human recombinant apolipoprotein A-1: comparison of three different expression systems," Clinica Chimica Acta, 268(1-2):41-60 (1997).
Silvian, L. et al., "Artemin crystal structure reveals insights into heparan sulfate binding," Biochemistry 45(22):6801-12 (Jun. 2006).
Skolnick et al. "From genes to protein structure and function: novel applications of computational approaches in the genomic era," Trends in Biotech., 18(1):34-39 (2000).
Sloot et al., "Detection of salicylate and its hydroxylated adducts 2.3- and 2.5-dihydroxybenzoic acids as possible indices for in vivo hydroxyl radical formation in combination with catechol- and indoleamines and their metabolites in cerebrospinal fluid and brain tissue," J. Neurosci. Meth., 60:141-149 (1995).
Smith et al. "The challenges of genome sequence annotation" or "The devil is in the details," Nature Biotechnology, 15:1222-1223 (1997).
Snider et al., "Tackling pain at the source: new ideas about nociceptors," Neuron 20:629-632 (Apr. 1998).
Stokes, B.T. et al., "Experimental modeling of human spinal cord injury: a model that crosses the species barrier and mimics the spectrum of human cytopathology," Spinal Cord 49:101-109 (2002).
Stoppini et al., "A simple method for organotypic cultures of nervous tissue," J. Neurosci. Methods, 37:173-182 (1991).
Talac, R. et al., "Animal models of spinal cord injury for evaluation of tissue engineering treatment strategies," Biomaterials 25:1505-1510 (2004).
Thompson et al., "The ClustalX windows interface: flexible strategies for multiple sequence alignment aided by quality analysis tools," Nucl. Acids Res., 25:4876-4882 (1997).
Trupp et al., "Peripheral expression and biological ctivities of GDNF, a new neurotrophic factor for avian and mammalian peripheral neurons," The Journal of Cell Biology 130(1):137-148 (Jul. 1995).
Tseng et al., "Neurturin protects dopaminergic neurons following medial forebrain bundle axotomy," Mol. Neurosci, 9:1817-1822 (1998).
Ulbrecht, J.S., et al., "Foot Problems in Diabetes: An Overview," Clinical Infectious Diseases (2004), 39:S73-82.
Unsicker, "GDNF: a cytokine at the interface of TGF-betas and neurotrophins," Cell Tissue Res., 286:175-178 (1996).
Vallejo et al., "Optimized procedure for renaturation of recombinant human bone morphogenetic protein-2 at high protein concentration," Biotechnol. Bioeng., 85(6):601-609 (2004).
Varmus, "Gene therapy: Not ready for prime time," Nature Medicine, 2(1):7-8 (1996).
Verma et al., "Gene therapy—promises, problems and prospects," Nature, 389:239-242 (1997).
Verma, "Gene therapy: beyond 2000," Mol. Ther., 6:493 (2000).
Veronese et al., "Introduction and Overview of Peptide and Protein Pegylation," Advanced Drug Delivery Reviews, 54(4):453-456 (2002).
Vickers, "A vaccine against Alzheimer's disease: developments to date." Drugs Aging 19(7):487-94 (2002).
Von Schwedler et al., "Vif is crucial for human immunodeficiency virus type 1 proviral DNA synthesis in infected cells," J. Virol., 67:4945-4955 (1993).
Vukicevic et al., "Induction of nephrogenic mesenchyme by osteogenic protein 1 (bone morphogenetic protein 7)," PNAS USA, 93:9021-9026 (1996).
Wang et al., "Single-chain Fv with manifold N-glycans as bifunctional scaffolds for immunomolecules," Protein Eng., 11(12):1277-83 (1998).
Wang et al., "Animal and cellular models of chronic pain ," Adv. Drug Delivery Rev., 55:949-965 (2003).
Wang et al , "Inhibitory effect of endostatin expressed by human liver carcinoma SMMC7721 on endothelial cell proliferation in vitro," World Journal of Gastroenterology, 8(2):253-257 (2002).
Wang et al., "Persistent Restoration of sensory function by immediate or delayed systemic artemin after dorsal root injury," Nature Neurosci. 11(4):488-496 (2008).

(56) References Cited

OTHER PUBLICATIONS

Watabe et al., "Spontaneously immortalized adult mouse Schwann cells secrete autocrine and paracrine growth-promoting activities," J. Neurosci. Res., 41:279-90 (1995).

Wefstaedt et al., "Neurotrophic factors of the GDNF family and their receptors are detectable in spiral ganglion cells of normal hearing as well as of deafened rats," Laryngorhinootologie, 85(11):802-8 (2006) (English abstract only, see p. 807).

Wells, "Additivity of Mutational Effects in Proteins," Biochemistry, 29:8509-8517 (1990).

West et al., "Estimation of the Number of Somatostatin Neurons in the Striatum: An In Situ Hybridization Study Using the Optical Fractionator Method," J. Comp. Neurol., 370:11-22 (1996).

White et al., "Chemokines: integrators of pain and inflammation," Nat Rev. Drug discovery 4:834-844 (2005).

Yan, M. et al., "Two-amino acid molecular switch in an epithelial morphogen that regulates binding to two distinct receptors," Science 290:523-527 (2000).

Zufferey et al., "Multiply attenuated lentiviral vector achieves efficient gene delivery in vivo," Nat. Biotechnol., 15:871-875 (1997).

Choh, "β-Endorphin omission analogs: Dissociation of immunoreactivity from other biological activities," PNAS, (1990) 77(6):3211-14.

Connell, LA et al., "Somatosensory impairment after stroke: frequency of different deficits and their recovery," Clin. Rehabil. (2008); 22(8):758-767 (Abstract Only).

ELISA, Wikipedia entry, retrieved from http:en.wikipedia.org/wiki/ELISA on Mar. 5, 2013.

Kimball Introduction to Immunology (1983), MacMillan NY, p. 101-102.

Paveliev M., et al., "GDNF family ligands activate multiple events during axonal growth in mature sensory neurons," Molecular and Cellular Neuroscience (2004), 25(3):453-459.

|  | | 10 | 20 | 30 | 40 | 50 |
|---|---|---|---|---|---|---|
| Human Neubla... | 1 | MELGLGGLST | LSHCPWPRRQ | PALWPTLAAL | ALLSSVAEAS | LGSAPRSPAP |
| Mouse Neubla... | 1 | MELGLAEPTA | LSHCLRPRWQ | SAWWPTLAVL | ALLSCVTEAS | LDPMSRSPAA |
| Rat Neublastin | 1 | MELGLGEPTA | LSHCLRPRWQ | PALWPTLAAL | ALLSSVTEAS | LDPMSRSPAS |
| Human Neubla... | 51 | REGPPPVLAS | PAGHLPGGRT | ARWCSGRARR | PPPQPSRPAP | PPPAP----P |
| Mouse Neubla... | 51 | RDGPSPVLAP | PTDHLPGGHT | AHLCSERTLR | PPPQSPQPAP | PPPGPALQSP |
| Rat Neublastin | 51 | RDVPSPVLAP | PTDYLPGGHT | AHLCSERALR | PPPQSPQPAP | PPPGPALQSP |
| Human Neubla... | 97 | SALPRGGRAA | RAGGPGSRAR | AAGARGCRLR | SQLVPVRALG | LGHRSDELVR |
| Mouse Neubla... | 101 | PAALRGARAA | RAGTRSSRAR | TTDARGCRLR | SQLVPVSALG | LGHSSDELIR |
| Rat Neublastin | 101 | PAALRGARAA | RAGTRSSRAR | ATDARGCRLR | SQLVPVSALG | LGHSSDELIR |
| Human Neubla... | 147 | FRFCSGSCRR | ARSPHDLSLA | SLLGAGALRP | PPGSRPVSQP | CCRPTRYEAV |
| Mouse Neubla... | 151 | FRFCSGSCRR | ARSQHDLSLA | SLLGAGALRS | PPGSRPISQP | CCRPTRYEAV |
| Rat Neublastin | 151 | FRFCSGSCRR | ARSPHDLSLA | SLLGAGALRS | PPGSRPISQP | CCRPTRYEAV |
| Human Neubla... | 197 | SFMDVNSTWR | TVDRLSATAC | GCLG | | |
| Mouse Neubla... | 201 | SFMDVNSTWR | TVDHLSATAC | GCLG | | |
| Rat Neublastin | 201 | SFMDVNSTWR | TVDHLSATAC | GCLG | | |

Fig. 1

```
                              SEQUENCE LISTING

<160> NUMBER OF SEQ ID NOS: 12

<210> SEQ ID NO 1
<211> LENGTH: 113
<212> TYPE: PRT
<213> ORGANISM: Homo sapiens

<400> SEQUENCE: 1

Ala Gly Gly Pro Gly Ser Arg Ala Arg Ala Ala Gly Ala Arg Gly Cys
 1               5                  10                  15

Arg Leu Arg Ser Gln Leu Val Pro Val Arg Ala Leu Gly Leu Gly His
            20                  25                  30

Arg Ser Asp Glu Leu Val Arg Phe Arg Phe Cys Ser Gly Ser Cys Arg
        35                  40                  45

Arg Ala Arg Ser Pro His Asp Leu Ser Leu Ala Ser Leu Leu Gly Ala
    50                  55                  60

Gly Ala Leu Arg Pro Pro Pro Gly Ser Arg Pro Val Ser Gln Pro Cys
65                  70                  75                  80

Cys Arg Pro Thr Arg Tyr Glu Ala Val Ser Phe Met Asp Val Asn Ser
                85                  90                  95

Thr Trp Arg Thr Val Asp Arg Leu Ser Ala Thr Ala Cys Gly Cys Leu
                100                 105                 110

Gly

<210> SEQ ID NO 2
<211> LENGTH: 113
<212> TYPE: PRT
<213> ORGANISM: Artificial Sequence
<220> FEATURE:
<223> OTHER INFORMATION: Synthetically generated peptide

<400> SEQUENCE: 2

Ala Gly Gly Pro Gly Ser Arg Ala Arg Ala Ala Gly Ala Arg Gly Cys
 1               5                  10                  15

Arg Leu Arg Ser Gln Leu Val Pro Val Arg Ala Leu Gly Leu Gly His
            20                  25                  30

Arg Ser Asp Glu Leu Val Arg Phe Arg Phe Cys Ser Gly Ser Cys Glu
        35                  40                  45

Arg Ala Arg Ser Pro His Asp Leu Ser Leu Ala Ser Leu Leu Gly Ala
    50                  55                  60

Gly Ala Leu Arg Pro Pro Pro Gly Ser Arg Pro Val Ser Gln Pro Cys
65                  70                  75                  80

Cys Arg Pro Thr Arg Tyr Glu Ala Val Ser Phe Met Asp Val Asn Ser
                85                  90                  95

Thr Trp Arg Thr Val Asp Arg Leu Ser Ala Thr Ala Cys Gly Cys Leu
                100                 105                 110

Gly

<210> SEQ ID NO 3
<211> LENGTH: 113
<212> TYPE: PRT
<213> ORGANISM: Artificial Sequence
<220> FEATURE:
<223> OTHER INFORMATION: Synthetically generated peptide
```

<400> SEQUENCE: 3

Ala Gly Gly Pro Gly Ser Arg Ala Arg Ala Gly Ala Arg Gly Cys
1               5                   10                  15

Arg Leu Arg Ser Gln Leu Val Pro Val Arg Ala Leu Gly Leu Gly His
            20                  25                  30

Arg Ser Asp Glu Leu Val Arg Phe Arg Phe Cys Ser Gly Ser Cys Arg
        35                  40                  45

Glu Ala Arg Ser Pro His Asp Leu Ser Leu Ala Ser Leu Leu Gly Ala
    50                  55                  60

Gly Ala Leu Arg Pro Pro Gly Ser Arg Pro Val Ser Gln Pro Cys
65              70                  75                  80

Cys Arg Pro Thr Arg Tyr Glu Ala Val Ser Phe Met Asp Val Asn Ser
                85                  90                  95

Thr Trp Arg Thr Val Asp Arg Leu Ser Ala Thr Ala Cys Gly Cys Leu
            100                 105                 110

Gly

<210> SEQ ID NO 4
<211> LENGTH: 113
<212> TYPE: PRT
<213> ORGANISM: Artificial Sequence
<220> FEATURE:
<223> OTHER INFORMATION: Synthetically generated peptide

<400> SEQUENCE: 4

Ala Gly Gly Pro Gly Ser Arg Ala Arg Ala Gly Ala Arg Gly Cys
1               5                   10                  15

Arg Leu Arg Ser Gln Leu Val Pro Val Arg Ala Leu Gly Leu Gly His
            20                  25                  30

Arg Ser Asp Glu Leu Val Arg Phe Arg Phe Cys Ser Gly Ser Cys Arg
        35                  40                  45

Arg Ala Glu Ser Pro His Asp Leu Ser Leu Ala Ser Leu Leu Gly Ala
    50                  55                  60

Gly Ala Leu Arg Pro Pro Gly Ser Arg Pro Val Ser Gln Pro Cys
65              70                  75                  80

Cys Arg Pro Thr Arg Tyr Glu Ala Val Ser Phe Met Asp Val Asn Ser
                85                  90                  95

Thr Trp Arg Thr Val Asp Arg Leu Ser Ala Thr Ala Cys Gly Cys Leu
            100                 105                 110

Gly

<210> SEQ ID NO 5
<211> LENGTH: 113
<212> TYPE: PRT
<213> ORGANISM: Artificial Sequence
<220> FEATURE:
<223> OTHER INFORMATION: Synthetically generated peptide

<400> SEQUENCE: 5

Ala Gly Gly Pro Gly Ser Arg Ala Arg Ala Gly Ala Arg Gly Cys
1               5                   10                  15

Arg Leu Arg Ser Gln Leu Val Pro Val Arg Ala Leu Gly Leu Gly His
            20                  25                  30

Arg Ser Asp Glu Leu Val Arg Phe Arg Phe Cys Ser Gly Ser Cys Glu
        35                  40                  45

Glu Ala Arg Ser Pro His Asp Leu Ser Leu Ala Ser Leu Leu Gly Ala

Gly Ala Leu Arg Pro Pro Gly Ser Arg Pro Val Ser Gln Pro Cys
 65                  70                  75                  80

Cys Arg Pro Thr Arg Tyr Glu Ala Val Ser Phe Met Asp Val Asn Ser
                 85                  90                  95

Thr Trp Arg Thr Val Asp Arg Leu Ser Ala Thr Ala Cys Gly Cys Leu
            100                 105                 110

Gly

<210> SEQ ID NO 6
<211> LENGTH: 99
<212> TYPE: PRT
<213> ORGANISM: Artificial Sequence
<220> FEATURE:
<223> OTHER INFORMATION: Synthetically generated peptide

<400> SEQUENCE: 6

Gly Cys Arg Leu Arg Ser Gln Leu Val Pro Val Arg Ala Leu Gly Leu
  1               5                  10                  15

Gly His Arg Ser Asp Glu Leu Val Arg Phe Arg Phe Cys Ser Gly Ser
                 20                  25                  30

Cys Glu Glu Ala Arg Ser Pro His Asp Leu Ser Leu Ala Ser Leu Leu
             35                  40                  45

Gly Ala Gly Ala Leu Arg Pro Pro Gly Ser Arg Pro Val Ser Gln
 50                  55                  60

Pro Cys Cys Arg Pro Thr Arg Tyr Glu Ala Val Ser Phe Met Asp Val
 65                  70                  75                  80

Asn Ser Thr Trp Arg Thr Val Asp Arg Leu Ser Ala Thr Ala Cys Gly
                 85                  90                  95

Cys Leu Gly

<210> SEQ ID NO 7
<211> LENGTH: 104
<212> TYPE: PRT
<213> ORGANISM: Artificial Sequence
<220> FEATURE:
<223> OTHER INFORMATION: Synthetically generated peptide

<400> SEQUENCE: 7

Ala Ala Gly Ala Arg Gly Cys Arg Leu Arg Ser Gln Leu Val Pro Val
  1               5                  10                  15

Arg Ala Leu Gly Leu Gly His Arg Ser Asp Glu Leu Val Arg Phe Arg
                 20                  25                  30

Phe Cys Ser Gly Ser Cys Glu Glu Ala Arg Ser Pro His Asp Leu Ser
             35                  40                  45

Leu Ala Ser Leu Leu Gly Ala Gly Ala Leu Arg Pro Pro Gly Ser
 50                  55                  60

Arg Pro Val Ser Gln Pro Cys Cys Arg Pro Thr Arg Tyr Glu Ala Val
 65                  70                  75                  80

Ser Phe Met Asp Val Asn Ser Thr Trp Arg Thr Val Asp Arg Leu Ser
                 85                  90                  95

Ala Thr Ala Cys Gly Cys Leu Gly
            100

<210> SEQ ID NO 8
<211> LENGTH: 113
<212> TYPE: PRT
<213> ORGANISM: Artificial Sequence
<220> FEATURE:
<223> OTHER INFORMATION: Synthetically generated peptide

<400> SEQUENCE: 8

Ala Gly Gly Pro Gly Ser Arg Ala Arg Ala Ala Gly Ala Arg Gly Cys
1               5                   10                  15

Arg Leu Arg Ser Gln Leu Val Pro Val Arg Ala Leu Gly Leu Gly His
            20                  25                  30

Arg Ser Asp Glu Leu Val Arg Phe Arg Phe Cys Ser Gly Ser Cys Arg
        35                  40                  45

Glu Ala Glu Ser Pro His Asp Leu Ser Leu Ala Ser Leu Leu Gly Ala
    50                  55                  60

Gly Ala Leu Arg Pro Pro Gly Ser Arg Pro Val Ser Gln Pro Cys
65                  70                  75                  80

Cys Arg Pro Thr Arg Tyr Glu Ala Val Ser Phe Met Asp Val Asn Ser
                85                  90                  95

Thr Trp Arg Thr Val Asp Arg Leu Ser Ala Thr Ala Cys Gly Cys Leu
            100                 105                 110

Gly

<210> SEQ ID NO 9
<211> LENGTH: 113
<212> TYPE: PRT
<213> ORGANISM: Artificial Sequence
<220> FEATURE:
<223> OTHER INFORMATION: Synthetically generated peptide

<400> SEQUENCE: 9

Ala Gly Gly Pro Gly Ser Arg Ala Arg Ala Ala Gly Ala Arg Gly Cys
1               5                   10                  15

Arg Leu Arg Ser Gln Leu Val Pro Val Arg Ala Leu Gly Leu Gly His
            20                  25                  30

Arg Ser Asp Glu Leu Val Arg Phe Arg Phe Cys Ser Gly Ser Cys Glu
        35                  40                  45

Arg Ala Glu Ser Pro His Asp Leu Ser Leu Ala Ser Leu Leu Gly Ala
    50                  55                  60

Gly Ala Leu Arg Pro Pro Gly Ser Arg Pro Val Ser Gln Pro Cys
65                  70                  75                  80

Cys Arg Pro Thr Arg Tyr Glu Ala Val Ser Phe Met Asp Val Asn Ser
                85                  90                  95

Thr Trp Arg Thr Val Asp Arg Leu Ser Ala Thr Ala Cys Gly Cys Leu
            100                 105                 110

Gly

<210> SEQ ID NO 10
<211> LENGTH: 220
<212> TYPE: PRT
<213> ORGANISM: Homo sapiens

<400> SEQUENCE: 10

Met Glu Leu Gly Leu Gly Gly Leu Ser Thr Leu Ser His Cys Pro Trp
1               5                   10                  15

Pro Arg Arg Gln Pro Ala Leu Trp Pro Thr Leu Ala Ala Leu Ala Leu
            20                  25                  30

Leu Ser Ser Val Ala Glu Ala Ser Leu Gly Ser Ala Pro Arg Ser Pro
        35                  40                  45

Ala Pro Arg Glu Gly Pro Pro Pro Val Leu Ala Ser Pro Ala Gly His

```
              50                  55                  60
Leu Pro Gly Gly Arg Thr Ala Arg Trp Cys Ser Gly Arg Ala Arg Arg
 65                  70                  75                  80

Pro Pro Pro Gln Pro Ser Arg Pro Ala Pro Pro Pro Ala Pro Pro
                 85                  90                  95

Ser Ala Leu Pro Arg Gly Gly Arg Ala Arg Ala Gly Gly Pro Gly
                100                 105                 110

Ser Arg Ala Arg Ala Ala Gly Ala Arg Gly Cys Arg Leu Arg Ser Gln
                115                 120                 125

Leu Val Pro Val Arg Ala Leu Gly Leu Gly His Arg Ser Asp Glu Leu
                130                 135                 140

Val Arg Phe Arg Phe Cys Ser Gly Ser Cys Arg Arg Ala Arg Ser Pro
145                 150                 155                 160

His Asp Leu Ser Leu Ala Ser Leu Leu Gly Ala Gly Ala Leu Arg Pro
                165                 170                 175

Pro Pro Gly Ser Arg Pro Val Ser Gln Pro Cys Cys Arg Pro Thr Arg
                180                 185                 190

Tyr Glu Ala Val Ser Phe Met Asp Val Asn Ser Thr Trp Arg Thr Val
                195                 200                 205

Asp Arg Leu Ser Ala Thr Ala Cys Gly Cys Leu Gly
                210                 215                 220

<210> SEQ ID NO 11
<211> LENGTH: 224
<212> TYPE: PRT
<213> ORGANISM: Mus musculus

<400> SEQUENCE: 11

Met Glu Leu Gly Leu Ala Glu Pro Thr Ala Leu Ser His Cys Leu Arg
  1               5                  10                  15

Pro Arg Trp Gln Ser Ala Trp Trp Pro Thr Leu Ala Val Leu Ala Leu
                 20                  25                  30

Leu Ser Cys Val Thr Glu Ala Ser Leu Asp Pro Met Ser Arg Ser Pro
                 35                  40                  45

Ala Ala Arg Asp Gly Pro Ser Pro Val Leu Ala Pro Pro Thr Asp His
 50                  55                  60

Leu Pro Gly Gly His Thr Ala His Leu Cys Ser Glu Arg Thr Leu Arg
 65                  70                  75                  80

Pro Pro Pro Gln Ser Pro Gln Pro Ala Pro Pro Pro Gly Pro Ala
                 85                  90                  95

Leu Gln Ser Pro Pro Ala Ala Leu Arg Gly Ala Arg Ala Ala Arg Ala
                100                 105                 110

Gly Thr Arg Ser Ser Arg Ala Arg Thr Thr Asp Ala Arg Gly Cys Arg
                115                 120                 125

Leu Arg Ser Gln Leu Val Pro Val Ser Ala Leu Gly Leu Gly His Ser
                130                 135                 140

Ser Asp Glu Leu Ile Arg Phe Arg Phe Cys Ser Gly Ser Cys Arg Arg
145                 150                 155                 160

Ala Arg Ser Gln His Asp Leu Ser Leu Ala Ser Leu Leu Gly Ala Gly
                165                 170                 175

Ala Leu Arg Ser Pro Pro Gly Ser Arg Pro Ile Ser Gln Pro Cys Cys
                180                 185                 190

Arg Pro Thr Arg Tyr Glu Ala Val Ser Phe Met Asp Val Asn Ser Thr
                195                 200                 205
```

```
Trp Arg Thr Val Asp His Leu Ser Ala Thr Ala Cys Gly Cys Leu Gly
    210                 215                 220

<210> SEQ ID NO 12
<211> LENGTH: 224
<212> TYPE: PRT
<213> ORGANISM: Rattus norvegicus

<400> SEQUENCE: 12

Met Glu Leu Gly Leu Gly Glu Pro Thr Ala Leu Ser His Cys Leu Arg
1               5                   10                  15

Pro Arg Trp Gln Pro Ala Leu Trp Pro Thr Leu Ala Ala Leu Ala Leu
            20                  25                  30

Leu Ser Ser Val Thr Glu Ala Ser Leu Asp Pro Met Ser Arg Ser Pro
        35                  40                  45

Ala Ser Arg Asp Val Pro Ser Pro Val Leu Ala Pro Pro Thr Asp Tyr
    50                  55                  60

Leu Pro Gly Gly His Thr Ala His Leu Cys Ser Glu Arg Thr Leu Arg
65                  70                  75                  80

Pro Pro Pro Gln Ser Pro Gln Pro Ala Pro Pro Pro Gly Pro Ala
                85                  90                  95

Leu Gln Ser Pro Pro Ala Ala Leu Arg Gly Ala Arg Ala Ala Arg Ala
                100                 105                 110

Gly Thr Arg Ser Ser Arg Ala Arg Ala Thr Asp Ala Arg Gly Cys Arg
            115                 120                 125

Leu Arg Ser Gln Leu Val Pro Val Ser Ala Leu Gly Leu Gly His Ser
    130                 135                 140

Ser Asp Glu Leu Ile Arg Phe Arg Phe Cys Ser Gly Ser Cys Arg Arg
145                 150                 155                 160

Ala Arg Ser Pro His Asp Leu Ser Leu Ala Ser Leu Leu Gly Ala Gly
                165                 170                 175

Ala Leu Arg Ser Pro Pro Gly Ser Arg Pro Ile Ser Gln Pro Cys Cys
            180                 185                 190

Arg Pro Thr Arg Tyr Glu Ala Val Ser Phe Met Asp Val Asn Ser Thr
            195                 200                 205

Trp Arg Thr Val Asp His Leu Ser Ala Thr Ala Cys Gly Cys Leu Gly
    210                 215                 220
```

COMPOSITIONS AND METHODS FOR INCREASING VASCULARIZATION

CROSS REFERENCE TO RELATED APPLICATIONS

This application is a divisional of U.S. application Ser. No. 12/598,293, filed on Jun. 8, 2010, issued as U.S. Pat. No. 8,329,655, which is a national phase filing under 35 U.S.C. §371 of International application number PCT/US2008/062265, filed May 1, 2008, which claims priority from provisional application No. 60/915,293 filed May 1, 2007. The entire content of the prior applications are incorporated herein by reference in their entirety.

TECHNICAL FIELD

The invention relates to protein chemistry, molecular biology, and vascular biology.

BACKGROUND

Neublastin, also known as artemin and enovin, is a 24 kDa homodimeric, secreted protein that promotes the outgrowth and survival of neurons of the peripheral and central nervous system (Baudet et al., 2000, *Development,* 127:4335; Masure et al., 1999, *Eur. J. Biochem.,* 266:892; Rosenblad et al., 2000, *Mol. Cell Neurosci.,* 15(2):199). Neublastin mRNA is expressed predominantly in embryonic kidney and lung, and in adults, is expressed highest in pituitary gland, trachea, and placenta (Baudet et al., 2000, *Development,* 127:4335).

Neublastin is a member of the glial cell line-derived neurotrophic factor (GDNF) ligand family. GDNF ligands activate both Ras and phosphatidylinositol-3-kinase signal transduction pathways by engaging the membrane-bound c-RET receptor tyrosine kinase. This c-RET-mediated signaling requires an additional co-receptor, a glycosylphosphatidyl inositol (GPI)-anchored GDNF family receptor alpha (GFRα) protein, which confers ligand specificity to c-RET. Four GFRα co-receptor proteins have been identified (GFRα1-4). Neublastin shows highest affinity for GFRα3 in vitro, however in studies using human fibroblasts, neublastin can stimulate c-RET-dependent signaling through either GFRα3 or GFRα1 (Baudet et al., 2000, Development, 127: 4335; Masure et al., 1999, *Eur. J. Biochem.* 266:892; Rosenblad et al., 2000, Mol. Cell Neurosci., 15(2):199).

Neublastin and the other GDNF family members are members of the transforming growth factor beta (TGF beta) superfamily and thus, are characterized by the presence of seven conserved cysteine residues with similar spacing which form the structure of a cysteine knot (Saarma, 1999, *Microsc. Res. Tech.,* 45:292). Each monomer contains two disulfide bonds that form a closed loop structure encircling the third disulfide to form a tight knot structure. The seventh cysteine contained within each monomer forms an intermolecular disulfide bond, covalently linking the monomers to form the final dimer product (Rattenholl et al 2000, *J. Mol. Biol.,* 305:523).

SUMMARY

The present invention is based, at least in part, on the discovery that administration of neublastin to a mammal promotes neovascularization and increased blood flow to ischemic muscle tissue following arterial occlusion.

In one aspect, the invention features a method of increasing vascularization in a tissue, which method includes the following steps: selecting a mammal exhibiting impaired or inadequate blood flow in a tissue (e.g., an ischemic tissue such as an ischemic muscle tissue); and administering to the mammal an amount of a polypeptide effective to increase vascularization in the tissue, wherein the polypeptide contains an amino acid sequence that is at least 80% identical to amino acids 15-113 of SEQ ID NO:1, and wherein the polypeptide, when dimerized, binds to a complex containing GFRalpha3 and RET. Also disclosed is the use of a polypeptide that contains an amino acid sequence that is at least 80% identical to amino acids 15-113 of SEQ ID NO:1, wherein the polypeptide, when dimerized, binds to a complex containing GFRalpha3 and RET for the preparation of a pharmaceutical composition for increasing vascularization in a tissue of a mammal exhibiting impaired or inadequate blood flow.

The amino acid sequence contained in the polypeptide of the methods and uses described herein can optionally be at least 90% identical (e.g., at least 95% or 98% identical) to amino acids 15-113 of SEQ ID NO:1. In some embodiments, the polypeptide contains or consists of amino acids 10-113 of SEQ ID NO:1, amino acids 15-113 of SEQ ID NO:1, amino acids 15-113 of SEQ ID NO:2, amino acids 15-113 of SEQ ID NO:3, amino acids 15-113 of SEQ ID NO:4, amino acids 15-113 of SEQ ID NO:5, amino acids 15-113 of SEQ ID NO:8, or amino acids 15-113 of SEQ ID NO:9. For example, the polypeptide can contain or consist of the amino acid sequence of SEQ ID NO:1, the amino acid sequence of SEQ ID NO:2, the amino acid sequence of SEQ ID NO:3, the amino acid sequence of SEQ ID NO:4, the amino acid sequence of SEQ ID NO:5, the amino acid sequence of SEQ ID NO:8, or the amino acid sequence of SEQ ID NO:9.

The polypeptide can be administered to the mammal, for example, via systemic administration (e.g., subcutaneous or intravenous administration) or local administration.

The tissue having impaired or inadequate blood flow can optionally be located in an extremity (e.g., hands or feet) of the mammal. In some embodiments, the tissue having impaired or inadequate blood flow contains a skin lesion (e.g., a skin lesion associated with a diabetic ulcer, such as a diabetic foot ulcer).

The mammal treated according to the methods and uses described herein can be, e.g., a human, a mouse, a rat, a cow, a pig, a dog, a cat, or a monkey.

In some embodiments of the methods and uses described herein, the heart of the mammal exhibits impaired blood flow and administration of the polypeptide increases vascularization of the heart, the mammal has suffered a stroke and exhibits impaired or inadequate blood flow in the tissue as a result of the stroke, the mammal has suffered a myocardial infarction and exhibits impaired or inadequate blood flow in the tissue as a result of the myocardial infarction, the mammal has a coronary artery disease and exhibits impaired or inadequate blood flow in the tissue as a result of the coronary artery disease, and/or the mammal has received a transplanted organ (e.g., a heart or dermis) and administration of the polypeptide increases vascularization in the transplanted organ.

A mammal treated according to the methods and uses described herein can have a disease or disorder such as an ischemic disease, a cardiovascular disease, and/or diabetes.

The methods and uses described herein can further include administering to the mammal one or more of an antithrombotic agent, a factor other than neublastin that increases vascularization, a cholesterol-lowering agent, a beta blocker, an anti-hypertensive agent, or an immunosuppressive agent.

The methods and uses described herein can further include determining whether increased vascularization has occurred subsequent to administration of the polypeptide.

In some embodiments of the methods and uses described herein, the mammal has not been diagnosed with a neurological disorder and/or has not been diagnosed with an ocular disorder.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, the exemplary methods and materials are described below. All publications, patent applications, patents, and other references mentioned herein are incorporated by reference in their entirety. In case of conflict, the present application, including definitions, will control. The materials, methods, and examples are illustrative only and not intended to be limiting.

Other features and advantages of the invention will be apparent from the following detailed description, and from the claims.

BRIEF DESCRIPTION OF THE DRAWINGS

FIG. 1 is an alignment of wild type human (SEQ ID NO:10), mouse (SEQ ID NO:11), and rat (SEQ ID NO:12) pre pro neublastin polypeptides. The left and right vertical lines indicate, respectively, the start of the mature 113 amino and 104 amino acid forms. The RRXR heparin binding motif is boxed.

DETAILED DESCRIPTION

Figure 2:
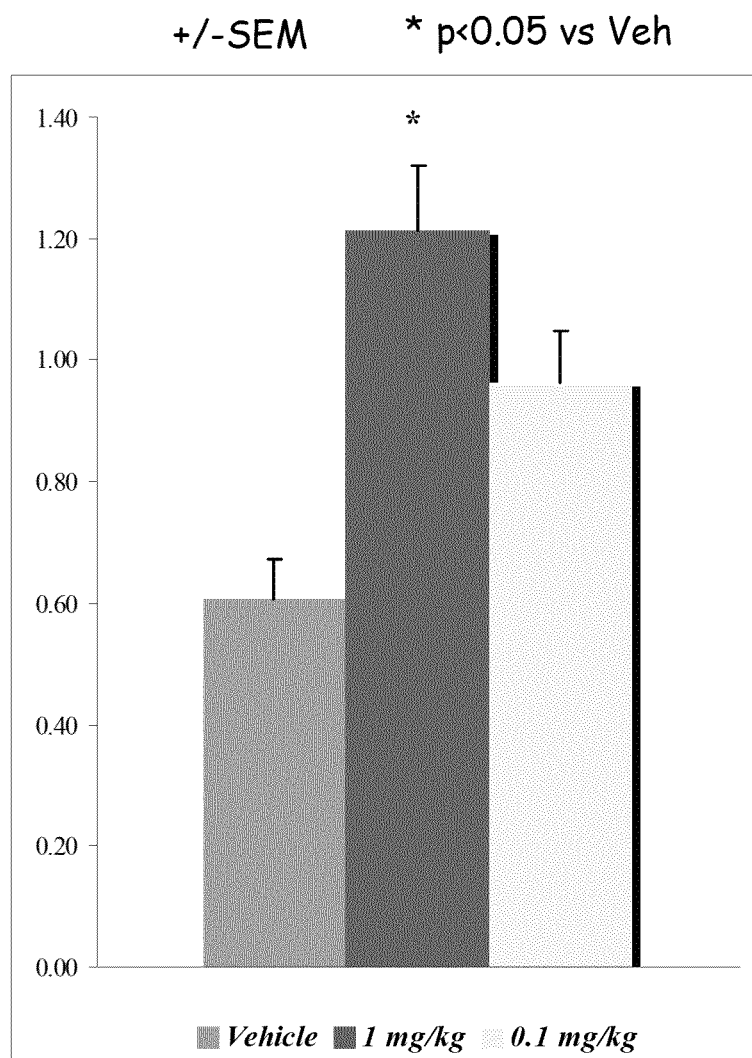
FIG. 2 is a bar graph depicting the effect of neublastin administration on post-ischemic vascularization in the mouse hindlimb. The Y-axis corresponds to capillary density, which is measured as the ratio of capillary number in the ischemic leg compared to a normal non-ischemic leg. "SEM" refers to standard error mean. P-values less than 0.05 (as compared to vehicle control) are indicated by "*."

The present invention provides compositions and methods for increasing vascularization in tissues exhibiting impaired or inadequate blood flow. As disclosed in the accompanying examples, administration of neublastin was found to promote neovascularization and increase blood flow to ischemic muscle tissue in a mammal.

Neublastin Polypeptides

Mature wild type human neublastin is 113 amino acids in length and has the following amino acid sequence: AGGPG-SRARAAGARGCRLRSQLVPVRALGLGHRSDELV RFRFCSGSCRRARSPHDLSLASLL-GAGALRPPPGSRPVSQPCCRPTRYEAVSFMDVNSTW RTVDRLSATACGCLG (SEQ ID NO:1). Polypeptides having the amino acid sequence of SEQ ID NO:1 or biologically active variants of thereof can be used in the methods described herein. A variant neublastin polypeptide can contain one or more additions, substitutions, and/or deletions, as detailed in the following sections. Wild-type neublastin polypeptides and biologically active variants thereof are collectively referred to herein as "neublastin polypeptides."

A variant neublastin polypeptide can vary in length from the corresponding wild-type polypeptide. Although the mature human neublastin polypeptide (SEQ ID NO:1) consists of the carboxy terminal 113 amino acids of pre pro neublastin (SEQ ID NO:10), not all of the 113 amino acids are required to achieve useful neublastin biological activity. Amino terminal truncation is permissible. Thus, a variant neublastin polypeptide can contain, for example, the carboxy terminal 99, 100, 101, 102, 103, 104, 105, 106, 107, 108, 109, 110, 111, 112, or 113 amino acids of SEQ ID NO:1 (i.e., its length can be 99, 100, 101, 102, 103, 104, 105, 106, 107, 108, 109, 110, 111, 112, or 113 amino acids).

A variant neublastin polypeptide can also vary in sequence from the corresponding wild-type polypeptide. In particular, certain amino acid substitutions can be introduced into the neublastin sequence without appreciable loss of a neublastin biological activity. In exemplary embodiments, a variant neublastin polypeptide (i) contains one or more amino acid substitutions, and (ii) is at least 70%, 80%, 85%, 90%, 95%, 98% or 99% identical to SEQ ID NO:1 (or 70%, 80%, 85%, 90%, 95%, 98% or 99% identical to amino acids 15-113 of SEQ ID NO:1). A variant neublastin polypeptide differing in sequence from SEQ ID NO:1 (or differing in sequence from amino acids 15-113 of SEQ ID NO:1) may include one or more amino acid substitutions (conservative or non-conservative), one or more deletions, and/or one or more insertions.

FIG. 1 is an alignment of the wild type human, mouse, and rat pre pro neublastin polypeptides. The vertical lines in FIG. 1 indicate the start of the mature 113 amino acid form (left vertical line) and 104 amino acid form (right vertical line) of neublastin. The RRXR heparin binding motif is boxed. This alignment of naturally occurring, bioactive forms of neublastin indicates specific exemplary residues (i.e., those that are not conserved among the human, mouse, and rat forms) that can be substituted without eliminating bioactivity.

Percent identity between amino acid sequences can be determined using the BLAST 2.0 program. Sequence comparison can be performed using an ungapped alignment and using the default parameters (Blossom 62 matrix, gap existence cost of 11, per residue gap cost of 1, and a lambda ratio of 0.85). The mathematical algorithm used in BLAST programs is described in Altschul et al., 1997, *Nucleic Acids Research* 25:3389-3402.

A conservative substitution is the substitution of one amino acid for another with similar characteristics. Conservative substitutions include substitutions within the following groups: valine, alanine and glycine; leucine, valine, and isoleucine; aspartic acid and glutamic acid; asparagine and glutamine; serine, cysteine, and threonine; lysine and arginine; and phenylalanine and tyrosine. The non-polar hydrophobic amino acids include alanine, leucine, isoleucine, valine, proline, phenylalanine, tryptophan and methionine. The polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Any substitution of one member of the above-mentioned polar, basic or acidic groups by another member of the same group can be deemed a conservative substitution.

Non-conservative substitutions include those in which (i) a residue having an electropositive side chain (e.g., Arg, His or Lys) is substituted for, or by, an electronegative residue (e.g., Glu or Asp), (ii) a hydrophilic residue (e.g., Ser or Thr) is substituted for, or by, a hydrophobic residue (e.g., Ala, Leu, Ile, Phe or Val), (iii) a cysteine or proline is substituted for, or by, any other residue, or (iv) a residue having a bulky hydrophobic or aromatic side chain (e.g., Val, Ile, Phe or Trp) is substituted for, or by, one having a smaller side chain (e.g., Ala, Ser) or no side chain (e.g., Gly).

A biologically active variant neublastin polypeptide, when dimerized, binds to a ternary complex containing GFRα3 and RET. Any method for detecting binding to this complex can be used to evaluate the biological activity a variant neublastin polypeptide. Exemplary assays for detecting the ternary complex-binding ability of a variant neublastin polypeptide are described in WO00/01815 (the content of which is incorporated herein by reference).

A variant neublastin polypeptide can also be assessed to evaluate its ability to trigger the neublastin signaling cascade. For example, the Kinase Receptor Activation (KIRA) assay can be used to assess the ability of a variant neublastin polypeptide to induce RET autophosphorylation (See also, Sadick et al., 1996, *Anal. Biochem.*, 235(2):207).

Substitutions at one or more of the following amino acid residues are expected to result in a variant neublastin polypeptide having reduced or absent heparin binding ability as compared to wild type neublastin: Arg 48, Arg 49, Arg 51, Ser 46, Ser 73, Gly 72, Arg 39, Gln 21, Ser 20, Arg 68, Arg 33, His 32, Val 94, Arg 7, Arg 9, or Arg 14. Reference to a neublastin amino acid reside by position number refers to the numbering of residues relative to SEQ ID NO:1. A neublastin amino acid residue designated for substitution (e.g., an arginine residue at position 48, 49, and/or 51) can be substituted with a non-conservative amino acid residue (e.g., glutamic acid) or a conservative or amino acid residue. Exemplary amino acids that can be substituted at a residue identified herein (e.g., position 48, 49, and/or 51) include glutamic acid, aspartic acid, and alanine.

Examples of variant neublastin polypeptides that exhibit reduced or absent heparin binding are disclosed in Table 1 and in WO 2006/023781 (the content of which is incorporated herein by reference). Amino acid residues of the variant neublastin polypeptides that are mutated as compared to the corresponding wild type position are bolded and underlined in Table 1. In addition, the neublastin polypeptide (e.g., 113, 99, or 104 amino acids in length) used as the background for the substitution is depicted in Table 1.

TABLE 1

Variant Neublastin Polypeptides

| SEQ ID NO | Position Substituted | Length of Polypeptide | Amino Acid Sequence |
|---|---|---|---|
| 2 | Arg 48 | 113 | AGGPGSRARAAGARGCRLRSQLVPVRA LGLGHRSDELVRFRFCSGSCERARSPHD LSLASLLGAGALRPPPGSRPVSQPCCRPT RYEAVSFMDVNSTWRTVDRLSATACGC LG |
| 3 | Arg 49 | 113 | AGGPGSRARAAGARGCRLRSQLVPVRA LGLGHRSDELVRFRFCSGSCREARSPHD LSLASLLGAGALRPPPGSRPVSQPCCRPT RYEAVSFMDVNSTWRTVDRLSATACGC LG |
| 4 | Arg 51 | 113 | AGGPGSRARAAGARGCRLRSQLVPVRA LGLGHRSDELVRFRFCSGSCRRAESPHD LSLASLLGAGALRPPPGSRPVSQPCCRPT RYEAVSFMDVNSTWRTVDRLSATACGC LG |
| 5 | Arg 48 and Arg 49 | 113 | AGGPGSRARAAGARGCRLRSQLVPVRA LGLGHRSDELVRFRFCSGSCEEARSPHD LSLASLLGAGALRPPPGSRPVSQPCCRPT RYEAVSFMDVNSTWRTVDRLSATACGC LG |
| 6 | Arg 48 and Arg 49 | 99 | GCRLRSQLVPVRALGLGHRSDELVRFRF CSGSCEEARSPHDLSLASLLGAGALRPPP GSRPVSQPCCRPTRYEAVSFMDVNSTW RTVDRLSATACGCLG |
| 7 | Arg 48 and Arg 49 | 104 | AAGARGCRLRSQLVPVRALGLGHRSDE LVRFRFCSGSCEEARSPHDLSLASLLGA GALRPPPGSRPVSQPCCRPTRYEAVSFM DVNSTWRTVDRLSATACGCLG |
| 8 | Arg 49 and Arg 51 | 113 | AGGPGSRARAAGARGCRLRSQLVPVRA LGLGHRSDELVRFRFCSGSCREAESPHD LSLASLLGAGALRPPPGSRPVSQPCCRPT RYEAVSFMDVNSTWRTVDRLSATACGC LG |
| 9 | Arg 48 and Arg 51 | 113 | AGGPGSRARAAGARGCRLRSQLVPVRA LGLGHRSDELVRFRFCSGSCERAESPHD LSLASLLGAGALRPPPGSRPVSQPCCRPT RYEAVSFMDVNSTWRTVDRLSATACGC LG |

A neublastin polypeptide can be optionally coupled to a polymer (e.g., a polyalkylene glycol moiety such as a polyethylene glycol moiety). In some embodiments, the polymer is coupled to the polypeptide at a site on the neublastin polypeptide that is an N terminus. In some embodiments, a variant neublastin polypeptide includes at least one amino acid substitution with respect to SEQ ID NO:1 (or with respect to amino acids 15-113 of SEQ ID NO:1), which provides an internal polymer conjugation site to which a polymer can be conjugated. In some embodiments, the polymer is coupled to a variant neublastin polypeptide at a residue (numbered in accordance with the sequence of SEQ ID NO:1) selected from the group consisting of position 14, position 39, position 68, and position 95. Exemplary neublastin variants that provide internal polymer conjugation sites are described in WO 02/060929 and WO 04/069176 (the contents of which are incorporated herein by reference).

A polypeptide can optionally contain heterologous amino acid sequences in addition to a neublastin polypeptide. "Heterologous," as used when referring to an amino acid sequence, refers to a sequence that originates from a source foreign to the particular host cell, or, if from the same host cell, is modified from its original form. Exemplary heterologous sequences include a heterologous signal sequence (e.g., native rat albumin signal sequence, a modified rat signal sequence, or a human growth hormone signal sequence) or a sequence used for purification of a neublastin polypeptide (e.g., a histidine tag).

Neublastin polypeptides can be isolated using methods known in the art. Naturally occurring or recombinantly produced neublastin polypeptides can be isolated from cells or tissue sources using standard protein purification techniques. Alternatively, mutated neublastin polypeptides can be synthesized chemically using standard peptide synthesis techniques. The synthesis of short amino acid sequences is well established in the peptide art. See, e.g., Stewart, et al., Solid Phase Peptide Synthesis (2d ed., 1984).

In some embodiments, neublastin polypeptides are produced by recombinant DNA techniques. For example, a nucleic acid molecule encoding a neublastin polypeptide can be inserted into a vector, e.g., an expression vector, and the nucleic acid can be introduced into a cell. Suitable cells include, e.g., mammalian cells (such as human cells or CHO cells), fungal cells, yeast cells, insect cells, and bacterial cells (e.g., *E. coli*). When expressed in a recombinant cell, the cell is preferably cultured under conditions allowing for expression of a neublastin polypeptide. The neublastin polypeptide can be recovered from a cell suspension if desired. As used herein, "recovered" means that the mutated polypeptide is removed from those components of a cell or culture medium in which it is present prior to the recovery process. The recovery process may include one or more refolding or purification steps. Buffers and methods for inducing folding of a denatured neublastin polypeptide are described in, e.g., WO 2006/023782.

Variant neublastin polypeptides can be constructed using any of several methods known in the art. One such method is site-directed mutagenesis, in which a specific nucleotide (or, if desired a small number of specific nucleotides) is changed in order to change a single amino acid (or, if desired, a small number of predetermined amino acid residues) in the encoded variant neublastin polypeptide. Many site-directed mutagenesis kits are commercially available. One such kit is the "Transformer Site Directed Mutagenesis Kit" sold by Clontech Laboratories (Palo Alto, Calif.).

Pharmaceutical Compositions

A neublastin polypeptide can be incorporated into a pharmaceutical composition containing a therapeutically effective amount of the polypeptide and one or more adjuvants, excipients, carriers, and/or diluents. Acceptable diluents, carriers and excipients typically do not adversely affect a recipient's homeostasis (e.g., electrolyte balance). Acceptable carriers include biocompatible, inert or bioabsorbable salts, buffering agents, oligo- or polysaccharides, polymers, viscosity-improving agents, preservatives and the like. One exemplary carrier is physiologic saline (0.15 M NaCl, pH 7.0 to 7.4). Another exemplary carrier is 50 mM sodium phosphate, 100 mM sodium chloride. Further details on techniques for formulation and administration of pharmaceutical compositions can be found in, e.g., REMINGTON'S PHARMACEUTICAL SCIENCES (Maack Publishing Co., Easton, Pa.).

Administration of a pharmaceutical composition containing a neublastin polypeptide can be systemic or local. Pharmaceutical compositions can be formulated such that they are suitable for parenteral and/or non-parenteral administration. Specific administration modalities include subcutaneous, intravenous, intramuscular, intraperitoneal, transdermal, intrathecal, oral, rectal, buccal, topical, nasal, ophthalmic, intra-articular, intra-arterial, sub-arachnoid, bronchial, lymphatic, vaginal, and intra-uterine administration.

Administration may be by periodic injections of a bolus of the pharmaceutical composition or may be made more continuous by intravenous or intraperitoneal administration from a reservoir which is external (e.g., an IV bag) or internal (e.g., a bioerodable implant, a bioartificial organ, or a colony of implanted neublastin production cells). See, e.g., U.S. Pat. Nos. 4,407,957, 5,798,113, and 5,800,828, each incorporated herein by reference. Administration of a pharmaceutical composition may be achieved using suitable delivery means such as: a pump (see, e.g., Annals of Pharmacotherapy, 27:912 (1993); Cancer, 41:1270 (1993); Cancer Research, 44:1698 (1984), incorporated herein by reference); microencapsulation (see, e.g., U.S. Pat. Nos. 4,352,883; 4,353,888; and 5,084,350, herein incorporated by reference); continuous release polymer implants (see, e.g., Sabel, U.S. Pat. No. 4,883,666, incorporated herein by reference); macroencapsulation (see, e.g., U.S. Pat. Nos. 5,284,761, 5,158,881, 4,976, 859 and 4,968,733 and published PCT patent applications WO92/19195, WO 95/05452, each incorporated herein by reference); injection, either subcutaneously, intravenously, intra-arterially, intramuscularly, or to other suitable site; or oral administration, in capsule, liquid, tablet, pill, or prolonged release formulation.

Examples of parenteral delivery systems include ethylene-vinyl acetate copolymer particles, osmotic pumps, implantable infusion systems, pump delivery, encapsulated cell delivery, liposomal delivery, needle-delivered injection, needle-less injection, nebulizer, aeorosolizer, electroporation, and transdermal patch.

Formulations suitable for parenteral administration conveniently contain a sterile aqueous preparation of the neublastin polypeptide, which preferably is isotonic with the blood of the recipient (e.g., physiological saline solution). Formulations may be presented in unit-dose or multi-dose form.

An exemplary formulation contains a neublastin polypeptide described herein and the following buffer components: sodium succinate (e.g., 10 mM); NaCl (e.g., 75 mM); and L-arginine (e.g., 100 mM).

Formulations suitable for oral administration may be presented as discrete units such as capsules, cachets, tablets, or lozenges, each containing a predetermined amount of the neublastin polypeptide; or a suspension in an aqueous liquor or a non-aqueous liquid, such as a syrup, an elixir, an emulsion, or a draught.

A neublastin polypeptide suitable for topical administration can be administered to a mammal (e.g., a human patient) as, e.g., a cream, a spray, a foam, a gel, an ointment, a salve, or a dry rub. A dry rub can be rehydrated at the site of administration. Neublastin polypeptides can also be in infused directly into (e.g., soaked into and dried) a bandage, gauze, or patch, which can then be applied topically. Neublastin polypeptides can also be maintained in a semi-liquid, gelled, or fully-liquid state in a bandage, gauze, or patch for topical administration (see, e.g., U.S. Pat. No. 4,307,717, the content of which is incorporated herein by reference).

Therapeutically effective amounts of a pharmaceutical composition may be administered to a subject in need thereof in a dosage regimen ascertainable by one of skill in the art. For example, a composition can be administered to the subject, e.g., systemically at a dosage from 0.01 µg/kg to 1000 µg/kg body weight of the subject, per dose. In another example, the dosage is from 1 µg/kg to 100 µg/kg body weight of the subject, per dose. In another example, the dosage is from 1 µg/kg to 30 µg/kg body weight of the subject, per dose, e.g., from 3 µg/kg to 10 µg/kg body weight of the subject, per dose.

In order to optimize therapeutic efficacy, a neublastin polypeptide can be first administered at different dosing regimens. The unit dose and regimen depend on factors that include, e.g., the species of mammal, its immune status, the body weight of the mammal. Typically, protein levels in tissue are monitored using appropriate screening assays as part of a clinical testing procedure, e.g., to determine the efficacy of a given treatment regimen.

The frequency of dosing for a neublastin polypeptide is within the skills and clinical judgement of physicians. Typically, the administration regime is established by clinical trials which may establish optimal administration parameters. However, the practitioner may vary such administration regimes according to the subject's age, health, weight, sex and medical status. The frequency of dosing may be varied depending on whether the treatment is prophylactic or therapeutic.

Methods of Treatment

The neublastin polypeptides described herein can be used for increasing vascularization in a mammal exhibiting impaired or inadequate blood flow in a tissue. For example, a neublastin polypeptide can be used to treat a mammal (e.g., a human) having, suspected of having, or at risk of developing, an ischemic disorder such as muscle ischemia, ischemic heart (e.g., resulting from myocardial infarction), a decubitus ulcer, ischemia resulting from varicose veins, ischemic complications of diabetes (e.g., a skin lesion such as a foot lesion), ischemic kidney, ischemic brain (e.g., resulting from a stroke), or ischemic liver. In addition, a neublastin polypeptide can be used to increase vascularization in a mammal that has received a transplanted organ and is in need of vascularization of the organ. Examples of specific medical conditions that can be treated or prevented by administration of a neublastin polypeptide are reviewed in the following sections.

(i) Stroke

Stroke (e.g., ischemic stroke, thrombotic stroke, embolic stroke, systemic hypoperfusion stroke, hemorrhagic stroke, intracerebral hemorrhage stroke, or subarachnoid hemorrhage stroke) is a disorder characterized by impaired or inadequate blood flow to one or more regions of the brain. The disturbance in perfusion can be venous, but is most often arterial. Loss or reduction of blood flow to the brain results in damage to ischemic areas, which can seriously impair local or global brain function. A neublastin polypeptide described herein can be administered (e.g., intravenously, subcutaneously, intranasally, or by intracranial local delivery) to a subject so as to increase blood flow to one or more regions of the brain to thereby prevent or reduce damage caused by a stroke. Where the subject is at risk of having a stroke (e.g., a subject diagnosed as having a partial occlusion of an artery in the brain), neublastin can be administered to the subject to prevent the occurrence, or lessen the severity, of a stroke.

Risk factors for developing a stroke include, for example, a family history of stroke, older age, race, hypertension, elevated cholesterol levels (particularly elevated LDL), smoking, diabetes, and obesity.

Stroke can be diagnosed or evaluated by, e.g., the severity and/or number of symptoms presented by a subject. Symptoms of stroke can vary depending the specific region of the brain that is affected. Stroke symptoms include, e.g., weakness (hemiplegia), numbness, reduction in sensory or vibratory sensation, altered senses (e.g., smell, taste, hearing, or vision (total or partial)), drooping of an eyelid (ptosis), decreased reflexes (e.g., gag, swallow), decreased sensation and muscle weakness of the face, balance problems, altered breathing, altered heart rate, aphasia (inability to speak or understand language), apraxia (altered voluntary movements), vertigo, and/or disequilibrium.

Stroke can also be diagnosed and evaluated (e.g., the severity of the stroke or the extent of the brain affected) using a variety of quantitative techniques including computed axial tomography (CAT), computed tomography (CT), or magnetic resonance imaging (MRI) scans. A medical professional can also use more qualitative diagnoses to diagnose or evaluate a subject having a stroke, e.g., by evaluating a subject's ability to smile, elevate one or both limbs, speak simple and/or complex sentences coherently, ability to walk or maintain balance, or any other symptoms of stroke described herein.

In addition to the administration of a neublastin polypeptide described herein, stroke can also be treated by a variety of techniques depending on the subject and the nature of the condition. Common treatments include mechanical thrombectomy or administration of tissue plasminogen activator (tPA) or other methods of thrombolysis.

(ii) Ischemic Heart Disease

Ischemic heart disease is characterized by impaired or insufficient blood flow to the heart muscle and can be caused by, e.g., atherosclerosis in one or more coronary arteries (coronary artery disease), cardiac arrhythmias, acute myocardial infarction, loss of heart muscle activity, or defective heart valves. Loss or reduction of blood flow to the heart results in damage to ischemic cardiac muscle tissue, which can cause permanent damage to the heart and/or death of the affected subject. A neublastin polypeptide described herein can be administered (e.g., intravenously, subcutaneously, or locally by myocardial or epicardial injection) to a subject so as to increase blood flow to one or more ischemic regions of the heart to thereby prevent or reduce damage caused by the ischemia. Where the subject is one at risk of developing ischemic heart disease, neublastin can be administered to prevent the occurrence, or lessen the severity, of cardiac ischemia.

Risk factors for developing ischemic heart disease include, e.g., poor diet, obesity, smoking, elevated and/or prolonged periods of stress, family history (e.g., a genetic predisposition), sedentary lifestyle, elevated cholesterol levels, and/or diabetes.

Ischemic heart disease can be diagnosed and/or evaluated by, e.g., the severity and/or number of symptoms of ischemic heart disease presented by the subject. Symptoms of ischemic heart disease vary and range in severity and include, but are not limited to, one or more of: chest pain, left arm pain, jaw pain, neck pain, back pain, sensation similar to heartburn, shortness of breath, pale skin, profuse sweating, weakness, light-headedness, nausea, vomiting, palpitations, and/or fatigue. Ischemic heart disease can be diagnosed or evaluated using a number of techniques known in the art, including electrocardiogram (ECG), coronary angiogram, chest radiograph, echocardiogram, and/or multiple gated acquisition (MUGA) scan. Ischemic heart disease can also be diagnosed or evaluated using biomarkers such as the level of one or more cardiac enzymes (e.g., creatine kinase, troponin I, and lactate dehydrogenase isozymes) in a subject's blood. Additional methods of diagnosing or evaluating a subject having ischemic heart disease include exercise stress test, wherein a subject's heart is monitored while the subject is exercising. The subject's heart rate, breathing, and blood pressure can be monitored. An ECG (above) can also be performed.

In addition to the administration of a neublastin polypeptide described herein, treatment for a subject having or suspected of having an ischemic heart disease can include administration of oxygen, acetylsalicylic acid (aspirin), glyceryl trinitrate, and pain relievers. Patients at risk of developing ischemic heart disease can be administered one or more of cholesterol lowering agents (e.g., statins), beta blockers, or anti-hypertensives (e.g., diuretics, angiotensin-converting enzyme inhibitors, vasodilators, or alpha blockers).

(iii) Ulcers

Ulcers are cutaneous lesions resulting from impaired or inadequate blood flow to the affected area (e.g., a foot). Such ulcers can be the result of vascular complications of diabetes (e.g., diabetic ulcers of the foot), venous insufficiency (crural ulcers), or excessive pressure (e.g., decubitus ulcers or bed sores). Loss or reduction of blood flow to an area of skin results in damage and/or death of that area of skin and surrounding tissue. A neublastin polypeptide described herein can be administered (e.g., topically administered to a subject's ulcer) to a subject so as to increase blood flow at the site of the ulcer or surrounding tissue, thereby reducing the severity or duration of the ulcer. Where the subject is at risk of developing an ulcer (for example, a paralyzed subject in a prolonged prone or supine position or a subject having cardiovascular complications due to diabetes), neublastin can be administered to the subject (e.g., by topical administration to the legs and feet of diabetic patients) to prevent the occurrence, or lessen the severity, of an ulcer.

Risk factors for developing cutaneous ulcers include, e.g., prolonged periods of sitting or laying (e.g., supine or prone positions), diabetes, varicose veins (see below), infection, and/or poor hygiene.

Methods for diagnosing and/or evaluating an ulcer on a subject include visual inspection, e.g., the appearance of the ulcer itself, redness, soreness, or pain. The visual inspection can also be used to check for symptoms indicative of the development of ulcers including, e.g., decreased sweating, dry skin and fissure formation, and propensity to develop infections at the affected area. Symptoms of decreased blood flow to the foot (and risk of developing foot ulcers, e.g., often resulting from complications from diabetes) include brittle nails, calluses, and hammer toes. The visual inspection can also include evaluating the size of the ulcer and/or whether or not the ulcer is infected. A medical professional can administer one or more tests to determine the level of blood flow to an area suspected of having impaired or inadequate blood flow including transcutaneous oxygen measurement (TCOM) and a nylon monofilament test. The TCOM requires the placement of electrodes directly onto the suspected area of skin. Generally a measured oxygen pressure of less than 40 mm Hg is an indication that the area is deficient in blood flow. The nylon monofilament test is a sensation test that involves the use of a 10 gauge nylon monofilament to gently prick the affected skin. The test is abnormal if the subject cannot sense the touch of the monofilament when it is pressed against the foot with just enough pressure to bend the filament.

In addition to the administration of a neublastin polypeptide described herein, treatments for cutaneous ulcers can involve surgery to remove dead or infected tissue and administration of antibiotics, where required.

(iv) Varicose Veins

Varicose veins (venous insufficiency) is a disorder characterized by an inability of the veins (generally of the legs) to transport deoxygenated blood back to the heart. Venous insufficiency can result from a thrombus (blood clot) or damage to, or loss of elasticity of, vein valves. A neublastin polypeptide described herein can be administered (e.g., topically to the subject's legs, subcutaneously, or intravenously to the affected veins) to a subject so as to increase blood flow to in the legs back to the heart, thereby reducing the severity of, or complications due to, varicose veins. Where the subject is at risk of developing varicose veins (e.g., a subject having one or more risk factors for varicose veins), neublastin can be administered to the subject to prevent the occurrence, or lessen the severity, of varicose veins.

Risk factors for developing varicose veins include, for example, old age, sex of the subject (women are more likely than men to develop varicose veins), family history (e.g., a genetic predisposition), obesity, and/or occupations that involve standing for prolonged periods of time.

Venous insufficiency can be diagnosed and/or evaluated in a subject by, e.g., the severity and/or number of symptoms presented by the subject including, e.g., pain or heaviness in the leg, feet and ankles, swelling, ulcers on the skin, or severe bleeding if the vein is injured. VI can be diagnosed or evaluated in a subject using a variety of techniques including duplex or Doppler Ultrasound, a non-invasive technique that uses ultrasound to visualize clots or other abnormalities in the blood vessels. Other methods of diagnosing/evaluating Venous insufficiency include CT Scan, venography, angiography such as X-ray or magnetic resonance angiography (MRA).

In addition to the administration of a neublastin polypeptide described herein, treatments for venous insufficiency can include, for example, laser surgery, sclerotherapy/microsclerotherapy, surgical vein stripping, ambulatory phlembectomy, and endoscopic vein surgery. Non-surgical therapies include, where venous insufficiency occurs in the legs, leg elevation, compression therapy (compression socks or leggings), exercise, weight loss, and skin care.

(v) Transplanted Organs

An organ transplant is a process in which a whole or partial organ is transferred from one subject to another subject. Transplanted organs include, e.g., heart, lung, liver, kidney, small bowel, pancreas, hand, digit (finger or toe), or skin (e.g., a skin graft such as a face transplant; see below). For an organ transplant to be successful, vascularization must occur between the transplanted organ and the host. Thus, a neublastin polypeptide described herein can be administered to a subject so as to promote vascularization between the transplanted organ and the host and increased blood flow to the transplanted organ, thereby preventing graft failure.

A common organ transplant is a skin graft, in which a region of dermis is surgically removed from one area of the body and transplanted to another. Skin grafts can be autologous (from the same subject) or can be heterologous (from a different subject). In some instances, the skin tissue can be obtained from an animal of a different species than the recipient subject (e.g., xenotransplantation). Skin grafts can be performed on a subject that has, e.g., suffered extensive burns or had cutaneous infections with areas of skin loss. In these cases, skin grafts are often used to minimize bacterial concentration at the site of skin loss and/or prevent loss of fluids. Skin grafts are also used in cosmetic surgeries, such as elective surgeries or those accompanying surgical procedures such as a mastectomy or chest wall reconstruction. Skin grafts can be extensive such as a whole or partial face transplant. As discussed above, for a skin graft to be successful, vascularization must occur between the graft site and the grafted tissue. Thus, a neublastin polypeptide described herein can be administered to a subject so as to promote vascularization between the grafted skin and the host to increase blood flow to the grafted skin, thereby preventing graft failure.

Monitoring the success of a skin graft can be performed a variety of ways including visual inspection, e.g., checking the color of the grafted skin, monitoring for a return of feeling to the grafted area, or monitoring the temperature of the grafted skin. Blood flow in a region or regions of the grafted skin can be measured directly, e.g., using laser Doppler perfusion monitoring (see below).

A subject suspected of having a disorder characterized by impaired or inadequate blood flow, as used herein, is a subject having one or more symptoms for a particular disorder characterized by impaired or inadequate blood flow (such as any of those described herein). For example, a subject suspected of having a stroke can be one having one or more symptoms of a stroke such as, but not limited to: weakness, numbness, drooping of an eyelid (ptosis), decreased reflexes (e.g., gag, swallow), decreased sensation and muscle weakness of the face, aphasia, apraxia, or any other symptoms described herein.

A subject at risk of developing a disorder characterized by impaired or inadequate blood flow, as used herein, is a subject having one or more risk factors of a particular disorder characterized by impaired or inadequate blood flow. For example, a subject at risk of developing ischemic heart disease can be subject with one or more risk factors for developing ischemic heart disease including, e.g., poor diet, obesity, smoking, elevated and/or prolonged periods of stress, sedentary lifestyle, elevated cholesterol levels, diabetes, or any other risk factors described herein.

A neublastin polypeptide can be administered to a subject in a variety of ways dependent, at least in part, on the type of disorder being treated and the location in the body of the impaired or inadequate blood flow. That is, in embodiments where a disorder is cutaneous in nature, such as a skin lesion, a decubitus ulcer, or a diabetic ulcer (e.g., diabetic foot ulcer), a neublastin polypeptide can be administered topically. For example, a neublastin polypeptide can be administered to the subject in a cream, salve, or ointment. Neublastin compositions described herein can also be infused into a bandage, gauze, or patch (see, e.g., U.S. Pat. No. 4,307,717). In embodiments where a disorder characterized by impaired or inadequate blood flow in a subject is internal (e.g., a stroke, ischemic heart disease, or organ transplant), neublastin can be administered to the subject intravenously, subcutaneously, or locally at the site where increased vascularization is needed. For example, neublastin can be administered to a transplanted kidney or heart and/or the surrounding host tissue during a transplant operation.

Combination Therapy

A neublastin polypeptide described herein can be administered to a subject as a monotherapy or as part of a multi-therapeutic regimen in conjunction with one or more additional agents that provide a therapeutic benefit to a subject having a disorder characterized by impaired or inadequate blood flow. For example, a neublastin polypeptide can be co-administered with an additional angiogenic factor such Angiogenin, Angiopoietin-1, Del-1, a fibroblast growth factor (e.g., aFGF, bFGF, or FGF2), Follistatin, Granulocyte Colony-Stimulating Factor (G-CSF), Hepatocyte Growth Factor (HGF), Interleukin-8 (IL-8), Leptin Midkine, Placental Growth Factor, Platelet-Derived Endothelial Cell Growth Factor (PD-ECGF), Platelet-Derived Growth Factor-BB (PDGF-BB), Pleiotrophin (PTN), Progranulin, Proliferin, Transforming Growth Factor-Alpha (TGF-alpha), Transforming Growth Factor-Beta (TGF-beta), Tumor Necrosis Factor-Alpha (TNF-alpha), and/or Vascular Endothelial Growth Factor (VEGF). In addition, a neublastin polypeptide can be administered in combination with one or more therapeutic agents that do not increase vascularization but are otherwise beneficial to a subject having a disorder characterized by impaired or inadequate blood flow. For example, a neublastin polypeptide can be co-administered with any one of an antithrombotic agent (e.g., aspirin, streptokinase, urokinase, tissue plasminogen activator, heparin, or hirudin), a pain medication, an antibiotic, a cholesterol lowering agent (e.g., a statin), a beta blocker, and/or an anti-hypertensive (e.g., a diuretic, an angiotensin-converting enzyme inhibitor, a vasodilator, or an alpha blocker). Where a neublastin polypeptide is used to increase vascularization of an organ that has been transplanted into a recipient (e.g., a transplanted heart, liver, kidney, lung, limb such as a finger, or dermis), the neublastin polypeptide can optionally be co-administered with one or more immunosuppressive agents.

The neublastin polypeptide and the one or more additional agents can be administered at the same time, the neublastin polypeptide can be administered first in time and the one or more additional agents administered second in time, or the one or more additional agents can be administered first in time and the neublastin polypeptide administered second in time.

Neublastin can optionally replace or augment a previously or currently administered therapy. For example, upon treating with a neublastin polypeptide, administration of the one or more additional agents can cease or diminish (e.g., be administered at lower levels). In some instances, a previous therapy can be maintained until the level of neublastin (e.g., the dosage or schedule) reaches a level sufficient to provide a therapeutic effect to the subject. In instances where a previous therapy is particularly toxic or poorly tolerated by a subject, administration of a neublastin polypeptide can be used to offset and/or lessen the amount of the previous therapy (e.g., an angiogenic therapy) to a level sufficient to give the same or improved therapeutic benefit, but without the toxicity.

In some instances where a subject is not responding to a first therapy, a subject can be administered neublastin. For example, if a subject (e.g., a human patient) is not responding to a first treatment such as VEGF (or another angiogenic factor described herein), a neublastin polypeptide can be administered to the subject. As used herein, a "subject not responsive to a treatment" refers to a patient in which treatment with one or more angiogenic therapies alone (i.e., not combined with neublastin) does not result in significant clinical improvement, more particularly does not result in a significant (and preferably long-term) improvement of the parameters used to measure angiogenic efficacy (such as but not limited to exercise treadmill testing (ETT or exercise stress test), angina time and angina frequency) (see, e.g., Fam et al. (2003) Circulation 108:2613). An example of such a group of subjects not responding to a VEGF angiogenic therapy is described by Henry et al. (2003) Circulation 107: 1359 1365.

Evaluating Efficacy of Treatments

The efficacy of a neublastin treatment can be evaluated by any of the methods described herein (e.g., by directly monitoring the level of new blood vessel growth or evaluating a particular feature or symptom of a disorder characterized by impaired or inadequate blood flow). For example, the amount or density of vasculature in a subject's brain can be measured (e.g., before and after treatment) using MRI (see, e.g., Dunn et al. (2004) Magn Reson. Med. 51(1):55-61) or ultrasound techniques such as adaptations of those described by Fosberg et al. (2004) Ultrasonics 42(1):325-330. The effect of neublastin treatment in promoting neovascularization can also be evaluated by monitoring an increase in blood flow using, e.g., laser Doppler techniques as described in, e.g., Freccero et al. (2003) Microvasc Res. 66(3):183-9; and Rendell et al. (1989) Diabetes 38(7):819-824. An exemplary device useful for measuring cutaneous blood flow by laser Doppler technique is the DRT4 (Moor Instruments, Devon, UK). Furthermore, the efficacy of neublastin to promote vascularization of a transplanted organ (e.g., a transplanted kidney, heart, or skin) can be measured by as an increase in transplanted organ function or an increase in organ health (e.g., by biopsy) following treatment.

The efficacy of a treatment can be assessed by evaluating a subject before and after treatment (e.g., comparing the oxygen tension in an affected area before or after treatment). Where progression of improvement in a disorder following one or more neublastin treatments is to be assessed, a subject can be evaluated at multiple time points following neublastin treatment (e.g., a one day, two day, and one week evaluation; a one week, one month, and six month evaluation; a one month, six month, and one year evaluation).

Where administration of neublastin is used to prevent the occurrence of a disorder characterized by impaired or inadequate blood flow (e.g., a lesion such as a foot ulcer due to vascular complications of diabetes), efficacy can be assessed as a delay in presentation of, or a failure to present, one or more symptoms of the disorder. The efficacy of a treatment over time in ameliorating one or more symptoms of a disorder can be determined by assessing, e.g., the number or severity of one or more symptoms at multiple time points following treatment. For example, a subject can have an initial assessment of the severity of his or her disorder, be administered a treatment, and then be assessed two or more times subsequent to the treatment (e.g., at one week and one month; at one month at two months; at two weeks, one month, and six months; or six weeks, six months, and a year). Where one or more neublastin treatments are administered to a subject for a limited period of time (e.g., a predetermined duration) or number of administrations, the effect of treatment on ameliorating one or more symptoms of a disorder characterized by impaired or inadequate blood flow can be assessed at various time points after the final treatment. For example, following the last administration of a dose of neublastin, the number or severity of a patient's symptoms can be assessed at 1 month (e.g., at 2 months, at 6 months, at one year, at two years, at 5 years or more) subsequent to the final treatment.

Animal Models of Disorders Characterized by Impaired or Inadequate Blood Flow

The Examples below describe an in vivo animal model system useful for studying the effect of neublastin treatment on an ischemic disorder. The efficacy of such treatment can be evaluated by direct analysis of the ischemic tissue, for example, by measuring capillary density in an ischemic muscle using immunohistochemistry techniques and/or measuring blood flow in a ischemic muscle. To evaluate prevention or delayed onset of a disorder characterized by impaired or inadequate blood flow, a neublastin polypeptide can also be administered to an animal before inducing the disorder. Additional animal models (e.g., mouse models) useful for evaluating the efficacy of neublastin treatments to increase vascularization include those described in, e.g., Couffinhal et al. (1988) Am J. Pathol. 152(6):1667-1679; Cao et al. (1998) Proc. Natl. Acad. Sci. USA 95(24):14389-14394; and Salven et al. (2002) FASEB J. 16:1471-1473. An animal model for impaired wound healing in diabetes is described in, e.g., Tsuboi et al. (1992) J. Dermatol. 19(11):673-75.

The following are examples of the practice of the invention. They are not to be construed as limiting the scope of the invention in any way.

EXAMPLES

Example 1

Neublastin Promotes Post-Ischemic Neovascularization

A murine model of hindlimb ischemia was used to determine if neublastin administration increases vascularization in mammals. Right femoral arteries of mice hindlimbs were surgically ligated. Neublastin was administered subcutaneously three times a week at a dosage of 1 milligram per kilogram (mg/kg) or 0.1 mg/kg. Alternatively, a set of mice were administered vehicle alone (no neublastin) as a control. Ten mice were evaluated in each group. Twenty one days (3 weeks) later, the mice were sacrificed and the gastrocnemius muscles were removed.

Vessel density was evaluated by high definition microangiography at the end of the treatment period, as described in Silvestre et al. (2005) Nat. Med. 11(5):499-506. Briefly, mice were anesthetized (isoflurane inhalation) and a contrast medium (Barium sulfate, 1 g/ml) was injected through a catheter introduced into the abdominal aorta. Images (two per animal) acquired by a digital X-ray transducer were assembled to obtain a complete view of the hindlimbs. The vessel density was expressed as a percentage of pixels per image occupied by vessels in the quantification area. Quantification zone was delineated by the place of the ligature on the femoral artery, the knee, the edge of the femur, and the external limit of the leg. Both dosages of neublastin increased the angiographic score in muscles from ischemic hindlimbs as compared to the vehicle-only control (FIG. 2). These results indicate that neublastin administration induces vascularization in ischemic tissue.

Example 2

Neublastin Promotes Post-Ischemic Cutaneous Blood Flow

To determine if neublastin treatment increases blood flow in ischemic tissue (e.g., skin), mouse femoral arteries were ligated as described above. Rat neublastin (the mature 113 amino acid form of the protein) was administered subcutaneously three times a week for three weeks at 1 mg/kg or 0.1 mg/kg. As a control, a set of mice were treated with vehicle alone.

Figure 3:
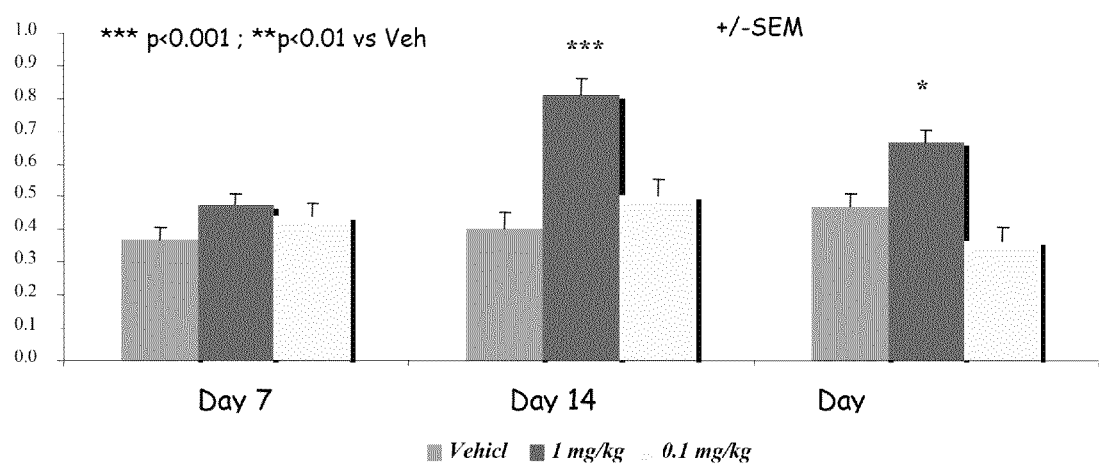
FIG. 3 is a bar graph depicting the effect of neublastin administration on post ischemic cutaneous blood flow. The Y-axis indicates blood flow as measured by the ratio of perfusion in the ischemic leg as compared to a normal non-ischemic leg. "SEM" refers to standard error mean. P-values less than 0.01 are indicated by "" and p-values less than 0.001 are indicated by "*."

At 7, 14, and 21 days, hair was removed from a small surface of ischemic hindlimb skin and the exposed tissue was evaluated for blood flow using laser Doppler perfusion monitoring as described in, e.g., Hisaka et al. (2004) J. Am. Coll. Cardiol. 43(10):1915-22. Measurements were performed in the paw only. An increase in cutaneous blood perfusion of ischemic limbs treated with neublastin was detected at 14 and 21 days (FIG. 3). These results indicate that neublastin administration results in increased blood flow in ischemic tissue.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of increasing vascularization in a tissue, the method comprising:
    selecting a human exhibiting impaired or inadequate blood flow in a tissue; and
    administering to the human an amount of a polypeptide effective to increase vascularization in the tissue, wherein the polypeptide comprises an amino acid sequence that is at least 80% identical to amino acids 15-113 of SEQ ID NO:1, wherein the polypeptide, when dimerized, binds to a complex containing GFRalpha3 and RET, and wherein the human has received a transplanted organ and administration of the polypeptide increases vascularization in the transplanted organ.

2. The method of claim 1, wherein the transplanted organ is a heart.

3. The method of claim 1, wherein the transplanted organ is dermis.

4. The method of claim 1, further comprising determining whether increased vascularization has occurred subsequent to administration of the polypeptide.

5. The method of claim 1, wherein the polypeptide is administered to the human via systemic administration.

6. The method of claim 1, wherein the polypeptide is administered to the human via subcutaneous administration.

7. The method of claim 1, wherein herein the polypeptide is administered to the human via local administration.

8. The method of claim 1, wherein the amino acid sequence is at least 90% identical to amino acids 15-113 of SEQ ID NO:1.

9. The method of claim 1, wherein the amino acid sequence is at least 95% identical to amino acids 15-113 of SEQ ID NO:1.

10. The method of claim 1, wherein the amino acid sequence is at least 98% identical to amino acids 15-113 of SEQ ID NO:1.

11. The method of claim 1, wherein the polypeptide comprises amino acids 15-113 of SEQ ID NO:1, amino acids 15-113 of SEQ ID NO:2, amino acids 15-113 of SEQ ID NO:3, amino acids 15-113 of SEQ ID NO:4, amino acids 15-113 of SEQ ID NO:5, amino acids 15-113 of SEQ ID NO:8, or amino acids 15-113 of SEQ ID NO:9.

12. The method of claim 1, wherein the polypeptide comprises the amino acid sequence of SEQ ID NO:1, the amino acid sequence of SEQ ID NO:2, the amino acid sequence of SEQ ID NO:3, the amino acid sequence of SEQ ID NO:4, the amino acid sequence of SEQ ID NO:5, the amino acid sequence of SEQ ID NO:8, or the amino acid sequence of SEQ ID NO:9.

13. The method of claim 1, wherein the polypeptide comprises amino acids 10-113 of SEQ ID NO:1.

14. The method of claim 1, wherein the human has not been diagnosed with a neurological disorder.

15. The method of claim 1, wherein the human has not been diagnosed with an ocular disorder.

\* \* \* \* \*